(12) United States Patent
Sahara et al.

(10) Patent No.: US 7,011,951 B1
(45) Date of Patent: Mar. 14, 2006

(54) APOPTOSIS-ASSOCIATED GENE

(75) Inventors: Setsuko Sahara, Osaka (JP); Yutaka Eguchi, Osaka (JP); Yoshihide Tsujimoto, Osaka (JP)

(73) Assignee: Shionogi & Co., LTD, Osaka (JP)

( * ) Notice: Subject to any disclaimer, the term of this patent is extended or adjusted under 35 U.S.C. 154(b) by 0 days.

(21) Appl. No.: 09/958,346

(22) PCT Filed: Apr. 7, 2000

(86) PCT No.: PCT/JP00/02254

§ 371 (c)(1),
(2), (4) Date: Jan. 28, 2002

(87) PCT Pub. No.: WO00/61743

PCT Pub. Date: Oct. 19, 2000

(30) Foreign Application Priority Data

Apr. 9, 1999 (JP) ................................. 11-103317

(51) Int. Cl.
*G01N 33/53* (2006.01)
(52) U.S. Cl. ...................... 435/7.1; 530/300; 530/350; 536/23.1; 435/7.21
(58) Field of Classification Search ................. 435/7.1, 435/6, 7.21; 530/350, 300; 514/2; 536/23.1
See application file for complete search history.

(56) References Cited

FOREIGN PATENT DOCUMENTS

WO    WO 98/54963 A2    12/1998
WO    WO9854963 A2 *    12/1998

OTHER PUBLICATIONS

Bowie et al (Science, 1990, 257 : 1306-1310).*
Burgess et al, (Journal of Cell Biology, 1990, 11: 2129-2138).*
Lazar et al. Molecular and cell Biology, 1988, 8: 1247-1252.*
Sambrook et al, eds, 1989, 2nd ed, Molecular Cloning, a laboratory manual, Cold Spring Harbor Laboratory Press, Cold Spring Harbor, p. 11.52.*
Oltvai et al, 1994, Cell, 79: 189-192.*
Gottschalk, AR et al, 1996, Cell Death and Differentiation, 3(1): 113-118.*
Vogel MW et al, 2002, Cerbellum, 1(4): 277-87.*
Xu Xin et al, 2001, FASEB J, 15(4): A313.*
Hummier E et al, 1994, PNAS, USA, 91: 5647-5661.*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Freshney (Culture of Animal Cells, A Manual of Basic Technique, Alan R. Liss, Inc., 1983, New York, p4).*
Dermer (Bio/Technology, 1994, 12:320).*
Ishikawa, R, 1998, DNA Res, 5: 169-176, and MPSRCH search report, us-09-958-346-4.rpr, p. 1.*
MPSRCH search report, 2004, us-09-958-348-4.rag, p. 3-4, and us-09-958-346-8.rng, p. 3-4.*
Database Genebank [online], "*Homo sapiens* mRNA for KIAA0670, partial cds." retrieved from NCBI Database accession No. AB014570 (Feb. 6, 1999).
Replaced Version—Database Genebank [online], "*Homo sapiens* mRNA for KIAA0670, partial cds." retrieved from NCBI Database accession No. AB014570 (Jan. 7, 2003).
Ishikawa et al, DNA Research, vol. 5, No. 3, pp. 169-176 (1998).
Sahara et al, Nature, vol. 401, pp. 168-173, ('1999).
Samejima et al, The Journal of Cell Biology, vol. 143, No. 1, pp. 225-239, (1998).
M. Enari et al., Nature, vol. 391, pp. 43-50, Jan. 1, 1998.
Database GSP Online EBI; Database Accession No. AAW88788, XP0022198190 (Abstract) corresponding to WO 98/54963, Dec. 10. 1998.
Database GSP Online EBI; Database Accession No. AAV84446, XP002219812 (Abstract) corresponding to WO 98/54963, Dec. 10, 1998.

* cited by examiner

*Primary Examiner*—Susan Ungar
*Assistant Examiner*—Minh-Tam Davis
(74) *Attorney, Agent, or Firm*—Birch, Stewart, Kolasch & Birch, LLP

(57) ABSTRACT

A polypeptide possessing an action of causing chromatin condensation; a sense nucleic acid encoding the polypeptide; an antisense nucleic acid thereof, a probe or primer capable of specifically binding to the nucleic acid; an antibody or a fragment thereof against the polypeptide; an agent for controlling apoptosis, comprising the nucleic acid, the polypeptide, or the antibody or a fragment thereof; a screening method for a substance for controlling chromatin condensation, comprising evaluating an activity of causing chromatin condensation exhibited by the polypeptide; and a substance for controlling chromatin condensation. The present invention is useful for screening a substance controlling apoptosis, its use for controlling apoptosis and its applications to various diseases accompanying apoptosis.

8 Claims, 16 Drawing Sheets

FIG. 4
-                 + Mono Q fraction
 

FIG. 5

```
MWRRKHPRTS  GGTRGVLSGN  RGVEYGSGRG  HLGTTEGRWR  KLPKMPEAVG  TDPSTSRKMA  ELEEVTLDGK  PLQALRVTDL    80
KAALEQRGLA  KSGQKSALVK  RLKGALMIEN  LQKHSTPHAA  FQPNSQIGEE  MSQNSFIKQY  LEKQQELLRQ  RLEREAREAA   160
ELEEASAESE  DEMIHPEGVA  SLLPPDFQSS  LERPELELSR  HSPRKSSSIS  EEKGDSDDEK  PRKGERRSSR  VRQARAAKLS   240
EGSQPAEEEE  DQETPSRNLR  VRADRNLKTE  EEEEEEEGDD  EDDEEEEGDD  EGQKSREAPI  LKEFKEEGEE  IPRVKPEEMM   320
DERPKTRSQE  QEVLERGGRF  TRSQEEARKS  HLARQQEKE   MKTTSPLEEE  EREIKSSQGL  KEKSKSPSPP  RLTEDRKKAS   400
LVALPEQTAS  EEETPPPLLT  KEASSPPPHP  QLHSEEEIEP  MEGPAPPVLI  QLSPPNTDAD  TRELLVSQHT  VQLVGGLSPL   480
SSPSDTKAES  PAEKVPEESV  LPLVQKSTLA  DYSAQKDLEP  ESDRSAQPLP  LKIEELALAK  GITEECLKQP  SLEQKEGRRA   560
SHTLLPSHRL  KQSADSSSSR  SSSSSSSSSR  SRSRSPDSSG  SRSHSPLRSK  QRDVAQARTH  ANPRGRPKMG  SRSTSESRSR   640
SRSRSRSASS  NSRKSLSPGV  SRDSSTSYTE  TKDPSSGQEV  ATPPVPQLQV  CEPKERTSTS  SSSVQARRLS  QPESAEKHVT   720
QRLQPERGSP  KKCEAEEAEP  PAATQPQTSE  TQTSHLPESE  RIHHTVEEKE  EVTMDTSENR  PENDVPEPPM  PIADQVSNDD   800
RPEGSVEDEE  KKESSLPKSF  KRKISVVSAT  KGVPAGNSDT  EGGQPGRKRR  WGASTATTQK  KPSISITTES  LKSLIPDIKP   880
LAGQEAVVDL  HADDSRISED  ETERNGDDGT  HDKGLKICRT  VTQVVPAEGQ  ENGQREEEEE  EKEPEAEPPV  PPQVSVEVAL   960
PPPAEHEVKK  VTLGDTLTRR  SISQQKSGVS  ITIDDPVRTA  QVPSPPRGKI  SNIVHISNLV  RPFTLGQLKE  LLGRTGTLVE  1040
EAFWIDKIKS  HCFVTYSTVE  EAVATRTALH  GVKWPQSNPK  FLCADYAEQD  ELDYHRGLLV  DRPSETKTEE  QGIPRPLHPP  1120
PPPPVQPPQH  PRAEQREQER  AVREQWAERE  REMERRERTR  SEREWDRDKV  REGPRSRSRS  RDRRRKERAK  SKEKKSEKKE  1200
KAQEEPPAKL  LDDLFRKTKA  APCIYWLPLT  DSQIVQKEAE  RAERAKEREK  RRKEQEEEEQ  KEREKEAERE  RNRQLEREKR  1280
REHSRERDRE  RERERERDRG  DRDRDRERDR  ERGRERDRRD  TKRHSRSRSR  STPVRDRGGR  R                      1341
```

FIG. 7

```
AcinusL: 1014  VHISNLVRPFTLGQLKELLIGRTSTLVEEAFWIDKI----RSHCFVTYSTVEEAVATRTHSEVKWPQSNPKFLCADYAEQ 1089
Sxl    :  205  LYVTNLPRTITDDQLDTIFGKYGSIVQKNILRDKLKGRPRGVAFVRYNKREEAQEAISNVL-IPEGGSQPLSVRLAEE  283
```

FIG. 9

APOPTOSIS-ASSOCIATED GENE

This application is the national phase under 35 U.S.C. § 371 of PCT International Application No. PCT/JP00/02254 which has an International filing date of Apr. 7, 2000, which designated the United States of America.

TECHNICAL FIELD

The present invention relates to an apoptosis-associated gene and a polypeptide, which are associated with the action mechanism of apoptosis, an agent for controlling apoptosis, a screening method for a substance for controlling chromatin-condensing activity, and the like.

BACKGROUND ART

In order that an organ or tissue functions normally in a living body, cell deaths of a part of cells as well as cell differentiation and cell proliferation are required. Most of such physiological cell deaths proceed due to apoptosis of which mechanism is usually strictly controlled.

Apoptosis is characterized by changes representatively including nuclear condensation and fragmentation of cells undergoing apoptosis, condensation and the fragmentation of the cells themselves, the fragmentation in the nucleosome unit (about 180 bp) of chromosomal DNA in the cells and the like.

For instance, in the formation process of an adult nematode (*C. elegans*), there is observed a phenomenon such that 131 cells die at a certain time in a certain site. In a mammal, it has also been known that a normal life event is maintained by the death of a certain cell at a certain time in the course of the development. These cell deaths are considered to be caused by apoptosis accompanied with morphological changes of the cells and the DNA fragmentation. Concretely, it has been shown that the cell deaths play an important role in the morphological formation during an individual development, the maintenance of a tissue homeostasis and the elimination of unwanted or hazardous cells.

Currently, studies on molecular mechanisms of apoptosis have been progressed. For instance, the studies on the action mechanisms of caspase-activated DNase [caspase-activated DNase (CAD)] and its inhibiting factor ICAD (inhibitor of CAD) in apoptosis have been made by the group of Nagata et al. [see, for instance, Enari, M., *Nature*, 391, 43–50 (1998) or the like]. Concretely, it is deduced that apoptosis signal causes an activation of cysteine protease caspase, and the resulting activated caspase then acts on CAD/ICAD complex (inactive form) to generate an active form CAD, and the active form CAD allows to fragmentate DNA into nucleosome unit, thereby resulting in cell death. Here, since the CAD synthesized in vitro in the absence of ICAD possesses no DNA-degrading activity, it is shown that the ICAD possesses a chaperonin function and is indispensable for the generation of the active form CAD.

Recently, it has been shown that the apoptosis is induced by a cancer-associated gene such as p53 antioncogene, c-myc or ras, an anti-cancer agent; irradiation with an ultraviolet or radioactive ray; or a certain cytokine representatively including Fas ligand, and the association with the signal transduction of apoptosis or the association with various diseases have come to a matter of interest.

However, studies on a target molecule for efficiently controlling apoptosis have not been sufficiently made at present.

DISCLOSURE OF INVENTION

An object of the present invention is to provide a polypeptide causing chromatin condensation without accompanying DNA fragmentation in nucleosome unit effective for controlling apoptosis, a sense or antisense nucleic acid encoding the polypeptide, an antibody against the polypeptide, and an agent for controlling apoptosis comprising the above-mentioned polypeptide, nucleic acid or antibody.

The gist of the present invention relates to:

[1] a polypeptide possessing an action of causing chromatin condensation, having a sequence selected from the group consisting of:
(A) the amino acid sequence of SEQ ID NO: 4; and
(B) an amino acid sequence having substitution, deletion, insertion or addition of at least one amino acid residue in the sequence of SEQ ID NO: 4;

[2] the polypeptide according to item [1] above, wherein the polypeptide possesses an action of causing chromatin condensation without accompanying DNA fragmentation;

[3] a sense nucleic acid selected from the group consisting of:
(a) a nucleic acid encoding a polypeptide consisting of the amino acid sequence of SEQ ID NO: 4;
(b) a nucleic acid having the nucleotide sequence of SEQ ID NO: 8;
(c) a nucleic acid encoding a polypeptide consisting of an amino acid sequence having substitution, deletion, insertion or addition of at least one amino acid residue in the sequence of SEQ ID NO: 4;
(d) a nucleic acid having a nucleotide sequence having substitution, deletion, insertion or addition of at least one base in the nucleotide sequence of SEQ ID NO: 8; and
(e) a nucleic acid capable of hybridizing to an antisense strand of a nucleic acid of any one of the above (a) to (d) under stringent conditions, wherein the sense nucleic acid encodes a polypeptide possessing an action of causing chromatin condensation;

[4] the sense nucleic acid according to item [3] above, wherein the polypeptide possesses an action of causing chromatin condensation without accompanying DNA fragmentation;

[5] a polypeptide encoded by a nucleic acid selected from the group consisting of:
(a) a nucleic acid encoding a polypeptide consisting of the amino acid sequence of SEQ ID NO: 4;
(b) a nucleic acid having the nucleotide sequence of SEQ ID NO: 8;
(c) a nucleic acid encoding a polypeptide consisting of an amino acid sequence having substitution, deletion, insertion or addition of at least one amino acid residue in the sequence of SEQ ID NO: 4;
(d) a nucleic acid having a nucleotide sequence resulting from substitution, deletion, insertion or addition of at least one base in the nucleotide sequence of SEQ ID NO: 8; and
(e) a nucleic acid capable of hybridizing to an antisense strand of a nucleic acid of any one of the above (a) to (d) under stringent conditions, wherein the polypeptide possesses an action of causing chromatin condensation;

[6] the polypeptide according to item [5] above, wherein the polypeptide possesses an action of causing chromatin condensation without accompanying DNA fragmentation;

[7] an antisense nucleic acid corresponding to the sense nucleic acid of item [3] or [4] above;

[8] a probe or primer capable of specifically binding to the sense nucleic acid of item [3] or [4] above, or to the antisense nucleic acid of item [7] above;

[9] an antibody or a fragment thereof against the polypeptide of item [1] or [2] above, or the polypeptide of item [5] or [6] above;

[10] an agent for controlling apoptosis, comprising the nucleic acid of any one of items [3], [4] and [7] above;

[11] an agent for controlling apoptosis, comprising the polypeptide of item [1] or [2] above, or the polypeptide of item [5] or [6] above;

[12] an agent for controlling apoptosis, comprising the antibody or a fragment thereof of item [9] above;

[13] a screening method for a substance for controlling chromatin-condensing activity, comprising the step of evaluating an activity of causing chromatin condensation exhibited by the polypeptide of item [1] or [2] above, or the polypeptide of item [5] or [6] above, in the presence of a substance to be tested;

[14] the screening method according to item [13] above, wherein an inhibition of an activity of causing chromatin condensation is evaluated;

[15] the screening method according to item [13] above, wherein an induction of expression of an activity of causing chromatin condensation is evaluated;

[16] the screening method according to item [13] above, wherein an enhancement of an activity of causing chromatin condensation is evaluated; and

[17] a substance for controlling chromatin-condensing activity, which can be screened by the screening method of any one of items [13] to [16] above.

BRIEF DESCRIPTION OF THE DRAWINGS

FIG. 4 is a photograph showing the nuclear changes caused by the MonoQ fraction. HeLa cells were permeabilized and incubated with or without a MonoQ column chromatography-active fraction (right panel) or in the absence of caspase-3.

FIG. 5 shows a deduced amino acid sequence of human Acinus L (SEQ ID NO: 1). In this figure, the sequences of four kinds of peptides obtained from purified bovine Acinus p17 are underlined. An open triangle indicates an amino terminal of Acinus p17. Also, in the figure, a caspase-3 cleavage site is indicated by a solid triangle, and a P-loop site is indicated by a double-underline.

FIG. 7 shows the results of the comparison between Acinus and Sx1 of *Drosophila* (SEQ ID NOS: 10 and 11). Identical amino acid residues and conserved amino acid residues are indicated by solid boxes and open boxes, respectively.

FIG. 9 shows the results of an in vitro cleavage of Acinus with caspase-3. Each of AcinusS and S (D/A) resulting from substitution of Asp$^{1093}$ with Ala was transiently expressed in COS-7 cells. Next, AcinusS was incubated in the presence or absence of 10 $\mu$M DEVD-CHO and in the presence or absence of caspase-3 (2.5 ng) for 1 hour, subjected to SDS-PAGE and immunoblotted with an anti-Acinus antibody. The full length AcinusS and a caspase-cleaved product are indicated by a white arrowhead and a black arrowhead, respectively.

BEST MODE FOR CARRYING OUT THE INVENTION

Figure 1:
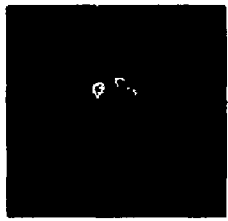
FIG. 1 is a photograph showing experimental results using an in vitro apoptosis system utilizing permeabilized HeLa cells. Permeabilized cells were incubated for 2 hours in the presence or absence of 0.1 mg/ml wheat germ agglutinin (WGA), an inhibitor of an active nuclear transport, by the use of an apoptotic Jurkat cell lysate (shown by "apoptosis" in the figure), a normal Jurkat cell lysate (shown by "normal" in the figure), a normal Jurkat cell lysate+ caspase-3, or only with the casepase-3. After staining with Hoechst 33342, the nuclear morphologies were examined with a fluorescent microscope.

In the present specification, the term "apoptosis" used herein means a way how cells die, characterized by changes representatively including condensation and fragmentation of nuclear chromatin of the cells, the condensation and the fragmentation of such cells themselves and the fragmentation of the chromosomal DNA in the nucleosome unit (about 180 bp) of the cells, including an event caused by a pathological factor such as a disease as well as a physiological factor (for example, expression of a physiological event such as immune, hormone action and development).

The above-mentioned morphological changes by apoptosis comprise the following stages. First, cells shrink and separate from adjacent cells, and chromatin, which is a complex of nuclear DNA with a protein, undergoes condensation in the periphery of the nuclear membrane, resulting in the nuclear condensation. At the same time, cilia on the cell surface disappear imparting a smoothened surface, and irregular projections appear and then cells are twisted and torn, to be fragmented into membrane-inclusion spherical apoptotic small bodies having various sizes. Subsequently, the resulting apoptotic small bodies are subjected to phagocytosis by phagocytic cells such as macrophage. The above-mentioned morphological changes are expressed following an identical morphological process regardless of the kinds of the cells, the kinds of the organisms or the inducing factors.

One of the significant features of the polypeptide of the present invention resides in that the polypeptide comprises a polypeptide sequence possessing an action for causing chromatin condensation. The chromatin condensation is caused without accompanying DNA fragmentation in nucleosome unit.

The evaluation of the chromatin condensation can be carried out by adding a standard assay mixture (5 μl) [composition: ATP generating system (composition: 1 mM ATP, 5 mM creatine phosphate and 20 units/ml creatine phosphate kinase), 1 mM GTP, 50 ng/ml recombinant caspase-3, 0.5 mg/ml importin α, 0.5 mg/ml importin β, 0.1 mg/ml Ran, 10 ng/ml p10, and the polypeptide (0.05 μg) of the present invention] to permeabilized HeLa cells or to 1 μl of permeabilized Jurkat cells (1×10⁶) on a plate, and then incubating the resulting mixture at 37° C. for 2 hours, and evaluating the nuclear changes under a fluorescent microscope after staining with 10 μM Hoechst 33342.

Also, the detection of DNA fragmentation can also be carried out as described by Enari et al. [Enari, M., *EMBO J.* 14, 5201–5208 (1995)].

In the preparation of the permeabilized HeLa cells which are used in the above-mentioned evaluation of the chromatin condensation, HeLa cells grown on a plate are subjected to a modified Adam's method [Adam et al., *J. Cell. Biol.* 111, 807–816 (1990)], whereby the permeability of HeLa cells can be improved. Concretely, the cells are washed with a transport buffer, treated with 20 μg/ml of digitonin (manufactured by Wako Pure Chemical Industries, Ltd.) for 3 minutes at room temperature, and then immersed in the transport buffer for 5 minutes, whereby the permeability can be improved. Also, in Jurkat cells, the permeability can be improved in accordance with the method of Gorlich et al. [Gorlich et al., *Cell* 79, 767–778 (1994)].

In the present specification, the phrase "polypeptide possessing an action for causing chromatin condensation"

means a polypeptide consisting of a part of the amino acid sequence of SEQ ID NO: 1, the polypeptide chain being capable of exhibiting an ability of causing chromatin condensation under conditions without proteolytic effect, for example, under the conditions in the absence of caspase-3 and in the presence of an inhibitor for inhibiting caspase. The polypeptide causing chromatin condensation described above can cause chromatin condensation without accompanying DNA fragmentation.

The polypeptide having the amino acid sequence of SEQ ID NO: 1 is a human Autholog of a factor which has been found for the first time in a HiTrap Q fraction of a bovine thymus cell lysate, and it has never been conventionally expected that a polypeptide sequence inducing apoptotic chromatin condensation exists in a part of the sequence. The associated factor of the polypeptide causing chromatin condensation is named Acinus (Apoptotic chromatin condensation inducer in the nucleus). Especially, a factor consisting of a polypeptide having the amino acid sequence of SEQ ID NO: 1 is designated as AcinusL.

It is suggested that in the downstream of an effector caspase-3, there are at least three different pathways as pathways involved in apoptotic changes in the nucleus, including (1) caspase-6 known as a lamin protease which breaks a nuclear membrane structure, (2) CAD/DEF40 causing an oligonucleosomal DNA cleavage and (3) Acinus inducing chromatin condensation without DNA fragmentation in oligonucleotide units, and thus provides a novel target in the control of apoptosis.

Figure 6:
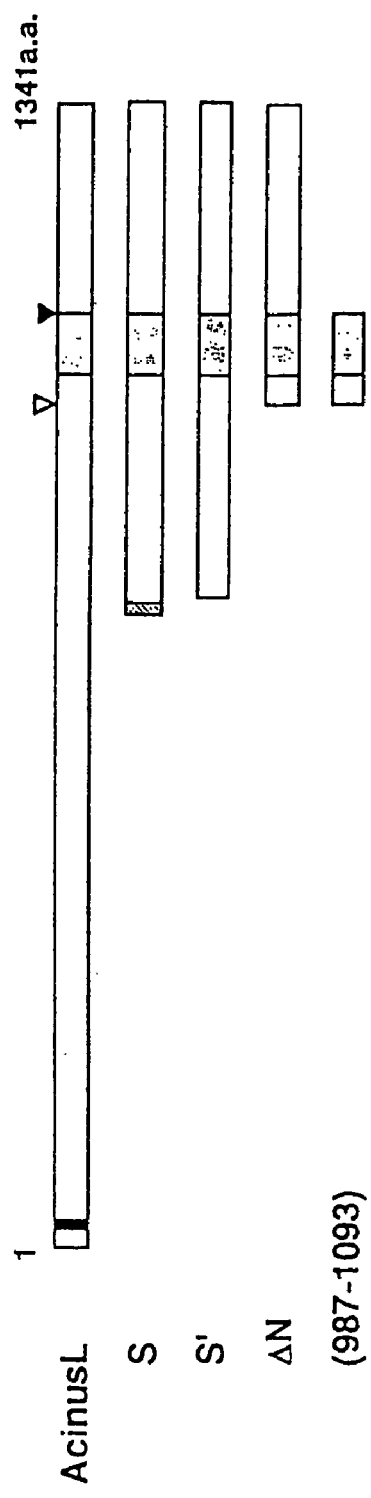
FIG. 6 is a schematic view showing Acinus. AcinusS has a unique sequence (MLSESKEG: hatched box)(SEQ ID NO: 9) at N-terminal subsequent to 767–1341 residues of AcinusL. AcinusS' corresponds to 774–1341 residues of the AcinusL. $\Delta$N and Acinus (987–1093) correspond to 987–1341 residues and 987–1093 residues, respectively, of the AcinusL. P-loop and the region homologous to RNA recognition motifs of Sx1 are indicated by a solid box and a dotted box, respectively.

The above-mentioned phrase "polypeptide possessing an action of causing chromatin condensation" includes, for instance, Acinus derivative as indicated by (987–1093) in FIG. 6 [referred to as Acinus (987–1093)] and the like. Acinus (987–1093) mentioned above is a polypeptide having the amino acid sequence (SEQ ID NO: 4) of positions 987–1093 in the above-mentioned amino acid sequence of SEQ ID NO: 1, which can be said to be an active form polypeptide of Acinus, because the polypeptide causes chromatin condensation even in the absence of caspase-3 and in the presence of a caspase inhibitor. More concrete examples of the above-mentioned "polypeptide possessing an action of causing chromatin condensation" include a polypeptide possessing an action of causing chromatin condensation, having a sequence selected from the group consisting of the amino acid sequence of SEQ ID NO: 4, and an amino acid sequence having substitution, deletion, insertion or addition of at least one amino acid residue in the amino acid sequence of SEQ ID NO: 4. Among them, a polypeptide possessing an action of causing chromatin condensation without accompanying DNA fragmentation is preferred. The polypeptide can be selected by evaluating the characteristics in accordance with "evaluation for chromatin condensation" described above, and "detection for DNA fragmentation" described above as occasion demands.

In the present invention, the phrase "amino acid sequence having substitution, deletion, insertion or addition of at least one amino acid residue" may be a naturally occurring sequence, or it may be an artificially prepared sequence, for instance, a sequence prepared from a nucleic acid described below by means of genetic engineering techniques.

The number of substitution, deletion, insertion or addition of the above-mentioned amino acids may be such that the resulting polypeptide is a polypeptide possessing an action of causing chromatin condensation, more preferably a polypeptide possessing an action of causing chromatin condensation without accompanying DNA fragmentation.

Besides the above-mentioned polypeptide having the sequence of SEQ ID NO: 4, there may be considered a case where the polypeptide possessing an action of causing chromatin condensation exists among the polypeptides which can be produced by a mechanism existing in a living body, such as an RNA differential splicing or a proteolytic action from genomic DNA corresponding to a cDNA encoding the polypeptide consisting of the amino acid of SEQ ID NO: 1, and such a polypeptide is also encompassed by the present invention. The polypeptide can be selected by evaluating the characteristics in accordance with "evaluation for chromatin condensation" described above, and "detection for DNA fragmentation" described above as occasion demands.

Concretely, each of AcinusL mentioned above, AcinusS of SEQ ID NO: 2 and AcinusS' of SEQ ID NO: 3 is considered to be a precursor which can be converted in a living body into an active form by a differential splicing and/or an action of caspase-3.

Further, a polypeptide encoded by a nucleic acid capable of hybridizing to an antisense strand of any of the nucleic acids (a) to (d) described below under stringent conditions, the polypeptide possessing an action of causing chromatin condensation is also encompassed by the polypeptide of the present invention. The polypeptide can be selected by evaluating the characteristics in accordance with "evaluation for chromatin condensation" described above, and in combination with "detection for DNA fragmentation" described above as occasion demands.

The polypeptide of the present invention can be obtained by allowing to express a nucleic acid described below by a known method, and then performing a known separation method. Concrete examples thereof are given in Examples, which are not limitative to the Examples in any way.

The polypeptide of the present invention can be used, for instance, for screening for a substance capable of controlling the action of the polypeptide, screening for a substance controlling apoptosis and control of apoptosis described below.

One of the significant features of the nucleic acid of the present invention resides in that the nucleic acid encodes the above-mentioned polypeptide possessing an action of causing chromatin condensation. The above-mentioned polypeptide encoded by the nucleic acid can cause chromatin condensation without accompanying DNA fragmentation.

In the present specification, the term "nucleic acid" refers to genomic DNA, cDNA, RNA and a nucleic acid analog. Here, the term "nucleic acid analog" refers to bases constituting the nucleic acid, such as cytosine, guanine, thymine, adenine and uracil and/or those with modifications in the sugar backbone.

The "nucleic acid encoding the polypeptide causing chromatin condensation" includes cDNA of a sense strand encoding the polypeptide of the present invention causing chromatin condensation without accompanying the DNA fragmentation, a corresponding RNA, a nucleic acid analog sequence, and the like.

Concretely, the nucleic acid includes sense nucleic acids selected from the group consisting of:
(a) a nucleic acid encoding a polypeptide consisting of the amino acid sequence of SEQ ID NO: 4 (sequence corresponding to positions 987–1093 in the amino acid sequence of SEQ ID NO: 1);
(b) a nucleic acid having the nucleotide sequence of SEQ ID NO: 8;
(c) a nucleic acid encoding a polypeptide consisting of an amino acid sequence having substitution, deletion, insertion or addition of at least one amino acid residue in the sequence of SEQ ID NO: 4;
(d) a nucleic acid having a nucleotide sequence having substitution, deletion, insertion or addition of at least one base in the nucleotide sequence of SEQ ID NO: 8; and
(e) a nucleic acid capable of hybridizing to an antisense strand of a nucleic acid of any one of the above (a) to (d), under stringent conditions, wherein the sense nucleic acid encodes a polypeptide causing chromatin condensation.

The nucleic acid encoding a polypeptide consisting of an amino acid sequence having substitution, deletion, insertion or addition of at least one amino acid residue in the amino acid sequence, and the DNA having a nucleotide sequence having substitution, deletion, insertion or addition of at least one base in the nucleotide sequence can be prepared by the method described in *Molecular Cloning: A Laboratory Manual,* 2nd Ed. [Sambrook et al., *Molecular Cloning: A Laboratory Manual,* 2nd Ed., Cold Spring Harbor Laboratory Press (1989)] or the like, which can be prepared by, for instance, the method of site-directed mutagenesis, the PCR method, and the like. In the present invention, the number of substitution, deletion, insertion or addition of the amino acid may be such that the polypeptide to be expressed is within the scope of a polypeptide capable of generating a polypeptide causing chromatin condensation.

Further, the present invention also encompasses a nucleic acid capable of capable of hybridizing to an antisense strand of a nucleic acid mentioned above, under stringent conditions, so long as the polypeptide to be expressed possesses an action of causing chromatin condensation.

Here, the "stringent conditions" include hybridization conditions described in *Molecular Cloning: A Laboratory Manual,* 2nd Ed. or the like. Concretely, the hybridization conditions include conditions of carrying out heating at 42° C. in a solution containing 6×SSC, 0.5% SDS and a 50% formamide solution, and thereafter washing at 68° C. in a solution containing 0.1×SSC and 0.5% SDS.

Further, the present invention also encompasses a nucleic acid capable of generating the nucleic acid of any one of (a) to (e) mentioned above.

Here, the phrase "nucleic acid capable of generating a nucleic acid of any one of (a) to (e)" means a nucleic acid comprising a nucleic acid of any one of (a) to (e), and capable of generating the nucleic acid of any one of (a) to (e) by transcription of RNA to genomic DNA, splicing or the like.

Concrete examples thereof include sense nucleic acids selected from the group consisting of:
(f) a nucleic acid encoding a polypeptide consisting of the amino acid sequence of any one of SEQ ID NOs: 1 to 3;
(g) a nucleic acid having the nucleotide sequence of any one of SEQ ID NOs: 5 to 7;
(h) a nucleic acid encoding a polypeptide consisting of an amino acid sequence having substitution, deletion, insertion or addition of at least one amino acid residue in the amino acid sequence of any one of SEQ ID NOs: 1 to 3;
(i) a nucleic acid having a nucleotide sequence having substitution, deletion, insertion or addition of at least one amino acid residue in the nucleotide sequence of any one of SEQ ID NOs: 5 to 7; and
(e) a nucleic acid capable of hybridizing to an antisense strand of the nucleic acid of any one of the above (a) to (d) under stringent conditions, wherein the sense nucleic acid encodes a polypeptide capable of generating a polypeptide causing chromatin condensation without accompanying chromatin condensation. Incidentally, each of SEQ ID NOs: 5 to 7 mentioned above corresponds to human acinusL, acinusS and acinusS'.

Also, the present invention encompasses a nucleic acid capable of hybridizing to an antisense strand of the nucleic acid under stringent conditions, so long as the polypeptide to be expressed possesses an action of causing chromatin condensation.

The present invention also encompasses a polypeptide encoded by the nucleic acid of the present invention, so long as the resulting polypeptide is a polypeptide possessing an action of causing chromatin condensation.

Also, the present invention also encompasses an antisense nucleic acid corresponding to the above-mentioned sense nucleic acid.

The nucleic acid can be used for control of apoptosis described below, screening of an autholog originated from another organism or the like.

The polypeptide of the present invention can be mass-produced by expressing the nucleic acid (sense nucleic acid) of the present invention.

A protein resulting from expression of a nucleic acid can be produced on the bases of many textbooks and literatures, for instance, *Molecular Cloning: A Laboratory Manual,* 2nd Ed. mentioned above or the like. An expression plasmid capable of replicating thereof and functioning in host cell by adding a translation initiation codon in the upstream of the nucleic acid to be expressed and a translation stop codon to the downstream thereof, adding a regulatory gene such as a promoter sequence for regulating transcription (for instance, trp promoter, lac promoter, T7 promoter, SV40 early promoter), and incorporating the resulting gene in an appropriate vector (for instance, pBR322, pUC19, pSV SPORT1 or the like).

Next, the transformant cells are obtained by introducing an expression plasmid into appropriate host cells. The host cells include cells of a prokaryote such as *Escherichia coli,* a unicellular eucaryote such as an yeast, a multicellular eucaryote such as an insect and an animal, and the like. The method for incorporating a gene into a host cell includes calcium phosphate method, DEAE-dextran method, electric pulse method, and the like. The transformant produces a desired protein by culturing in an appropriate medium. The protein obtained as described above can be isolated and purified by a general biochemical method. In addition, in order to facilitate isolation and purification, there may be added a sequence which can be expressed as His tag, or GST fusion protein.

There is provided a probe or primer capable of specifically binding to the above-mentioned sense nucleic acid or antisense nucleic acid by the use of the nucleic acid of the present invention.

Here, the phrase "probe or primer capable of specifically binding to (the nucleic acid)" encompasses an oligonucleotide capable of hybridizing under the hybridization conditions which are suitable for the oligonucleotide to be used as the probe or primer.

The length of the above-mentioned probe or primer and the nucleotide sequence can be appropriately selected from the sequences of the nucleic acid of the present invention in consideration of the Tm values depending upon its purpose of use. It is desired that the length of the above-mentioned probe is 14 nucleotide length or more, preferably 18 nucleotide length or more, from the viewpoint of preventing nonspecific hybridization. In addition, it is desired that the length of the primer is, for instance, 15 to 40 nucleotide length, preferably 17 to 30 nucleotide length.

The above-mentioned probe or primer can be usually prepared by a method used in nucleic acid synthesis. For instance, the probe or primer can be prepared by chemical synthesis method representatively including phosphoramidite method, and an enzymatic synthesis method utilizing DNA polymerases.

In addition, the probe or primer can be prepared by fragmenting the nucleic acid of the present invention by an enzymatic treatment with a restricted endonuclease, and various nucleases, or a short physical treatment representatively including sonication treatment, and isolating the resulting fragment.

The conditions for the specific binding in the above-mentioned probe or primer include the hybridization conditions described in *Molecular Cloning: A Laboratory Manual*, 2nd Ed. mentioned above or the like. Such conditions include, for instance, conditions of 0.1×SSC and 65° C. in a case of a sufficiently long nucleotide; and conditions of 6×SSC and 25° C. in a case of a short nucleotide; and the like.

The above-mentioned probe or primer is thought to be applied to screening of various libraries (genomic DNA or cDNA), pharmaceuticals, research reagents, and the like.

The antibody of the present invention is not particularly limited, so long as the antibody possesses an ability of specifically binding to Acinus, which is the concrete polypeptide of the present invention. The antibody may be any of polyclonal antibodies and monoclonal antibodies, and it may be a fragment thereof. Further, antibodies modified by known techniques and antibody derivatives, for instance, humanized antibody, Fab fragment, single-chain antibody, and the like can be also used. The antibody of the present invention can be readily prepared by appropriately immunizing a rabbit, a mouse or the like using all or a part of the polypeptide of the present invention in accordance with the method described in, for instance, *Current Protocols in Immunology*, edited by John E. Coligan, published by John Wiely & Sons, Inc., 1992. In addition, the antibody can be prepared by genetic engineering means. In addition, the antibody encompasses an antibody capable of specifically binding to a partial fragment of the polypeptide, or a fragment thereof.

The resulting antibody is purified and thereafter treated with a peptidase or the like, thereby giving an antibody fragment. The use of the resulting antibody or a fragment thereof includes applications to affinity chromatography, screening of various kinds of libraries (genomic DNA or cDNA), pharmaceuticals, research reagents, and the like.

Further, when the antibody of the present invention is used in enzyme immunoassay, fluorescent immunoassay or luminescent immunoassay, the antibody may also be modified in various ways for the purpose of facilitating the detection.

According to the present invention, there may further be provided an agent for controlling apoptosis.

One of the significant features of the agent for controlling apoptosis of the present invention resides in that the agent for controlling apoptosis comprises the polypeptide, the nucleic acid or the antibody of the present invention. As described above, since the agent for controlling apoptosis comprises the polypeptide, the nucleic acid or the antibody, there is exhibited an excellent effect such that chromatin condensation in apoptosis can be suppressed or accelerated. The agent for controlling apoptosis of the present invention will be described below in individual embodiments of (1) an agent for controlling apoptosis comprising a polypeptide, (2) an agent for controlling apoptosis comprising a nucleic acid, (3) an agent for controlling apoptosis comprising an antibody, and (4) an embodiment other than the agents for controlling apoptosis of embodiments (1) to (3) described above.

(1) Agent for Controlling Apoptosis Comprising Polypeptide

In the agent for controlling apoptosis of the present invention, the polypeptide possessing an action of causing chromatin condensation of the present invention can be employed as it is, or in a form subjected to various modifications for facilitating the incorporation into a certain cell.

While an in vivo immune response may sometimes be caused when an agent for controlling apoptosis comprising the polypeptide is employed, various aids for reducing the immune response may be added within the range such that the polypeptide of the present invention exhibits an action for causing chromatin condensation.

(2) Agent for Controlling Apoptosis Comprising Nucleic Acid

In the agent for controlling apoptosis of the present invention, a sense nucleic acid and an antisense nucleic acid can appropriately be selected depending upon the purpose of use.

For example, when the apoptosis takes place by causing the chromatin condensation, a sense nucleic acid is used. On the other hand, when apoptosis is suppressed by suppressing chromatin condensation, an antisense nucleic acid is used.

The method of administering the agent for controlling apoptosis comprising the sense nucleic acid of the present invention to be introduced into cells includes a method of administering a construct resulting from incorporation of the nucleic acid into a viral vector as the agent for controlling apoptosis.

The viral vector includes, for instance, RNA viruses and DNA viruses such as retrovirus, adenovirus, adeno-associated virus, herpes virus, vaccinia virus, pox virus, polio virus, Sindbis virus, and the like.

Other methods include a method of directly intramuscularly administering an agent for controlling apoptosis comprising an expression plasmid harboring a sense nucleic acid of the present invention (DNA vaccine method), a liposome method, a lipofectin method, a microinjection method, a potassium phosphate method, an electroporation method and the like.

The agent for controlling apoptosis can be administered via a suitable administration route depending on the target of which apoptosis is to be controlled. For example, the agent for controlling apoptosis can be intravenously, arterially, subcutaneously or intramuscularly administered. When the agent is administered by in vivo method, the agent can, for instance, take a form of preparations such as liquid preparations. In general, the agent takes the form of an injection or the like comprising the nucleic acid of the present invention as an active ingredient, and a conventional vehicle may be added thereto as occasion demands. In a liposome or membrane fusion liposome comprising the nucleic acid of the present invention (such as Sendai virus (HVJ)-liposome), the agent can take a form of liposome preparations such as suspensions, cryogens and centrifugally-concentrated cryogens.

The content of the nucleic acid of the present invention in the preparation can be properly adjusted depending on the target of which apoptosis is to be controlled.

When the antisense nucleic acid is employed, the antisense nucleic acid can, for instance, be prepared on the basis of the nucleotide sequence of the sense nucleic acid encoding the polypeptide of the present invention, or a corresponding antisense nucleic acid can be readily prepared by incorporating the sense nucleic acid into a gene expression plasmid in the antisense direction.

This antisense oligonucleotide may be a sequence complementary to any of the parts of the coding part or 5' non-coding part of a cDNA, which is the nucleic acid of the present invention. It is desired that the antisense oligonucleotide is a sequence complementary preferably to transcription initiation site, translation initiation site, 5' non-translation region or exon regions.

The term chemically-modified product of a nucleic acid refers to a chemically-modified product capable of enhancing transition ability or stability of DNA or RNA in a cell. The chemically-modified product includes, for instance, derivatives such as phosphothioate, phosphorodithioate, alkyl phosphotriesters, alkyl phosphonates, alkyl phosphoamidates and the like [*Antisense RNA and DNA*, published by WILEY-LESS, 1–50 (1992)]. This chemically-modified product can be prepared in accordance with the literature mentioned above.

When an expression plasmid into which an antisense nucleic is incorporated is used as an agent for controlling apoptosis, the agent for controlling apoptosis may be administered to a target by a method utilizing a liposome, a recombinant virus and the like. The expression plasmid of an antisense nucleic acid can be simply prepared by ligating the sense nucleic acid of the present invention in such a manner that a transcription is carried out in an opposite direction downstream of a promoter by using an usual expression vector.

To the agent for controlling apoptosis comprising an antisense nucleic acid or a chemically-modified form thereof as it is, various aids can be added, within the range such that the agent exhibits an action of causing chromatin condensation.

(3) Agent for Controlling Apoptosis Comprising Antibody

In the agent for controlling apoptosis comprising an antibody, various adjuvants may be contained so that Acinus in the cells can be depleted. Its preparation form is not particularly limited and can be appropriately determined depending on the target of which apoptosis is to be controlled, the purpose of use, and the like. The content of the antibody of the present invention in the agent for controlling apoptosis can be appropriately determined depending on the target of which apoptosis is to be controlled.

Furthermore, a nucleic acid capable of expressing the antibody of the present invention in the cells can be prepared, and the resulting nucleic acid can be used similarly to the administration of the agent for controlling apoptosis comprising the nucleic acid mentioned above.

(4) Embodiment Other than Agents for Controlling Apoptosis of Embodiments (1) to (3)

Also, a substance for controlling the action of the polypeptide of the present invention can also be screened by using the polypeptide of the present invention or the like, and the resulting substance can also be used as the agent for controlling apoptosis of the present invention.

Further, a substance for controlling transcription and translation from the nucleic acid of the present invention, for instance, ribozyme, and a nucleic acid for forming a triple stranded-nucleic acid with a double-stranded DNA encoding a region encoding expression can also be used as the agent for controlling apoptosis of the present invention.

The term "ribozyme" refers to an RNA molecule possessing an activity of cleaving mRNA which encodes a certain protein, and inhibiting expression of the particular protein. The ribozyme can be designed on the basis of the nucleotide sequence encoding a certain protein. For instance, as a hammerhead ribozyme, one obtained by a method described in *FEBS Letter*, 228, 228–230 (1988) can be used. In addition to the hammerhead ribozyme, the ribozyme as referred to in the present specification encompasses any of those ribozymes, regardless of the kinds of the ribozymes, such as hairpin-shaped ribozymes and delta-shaped ribozymes, so long as the ribozyme is capable of cleaving mRNA of a particular protein, thereby inhibiting expression of the particular protein.

The nucleic acid for forming a triple-stranded nucleic acid with a double-stranded DNA encoding a region suppressing expression can be prepared by referring to, for instance, *Nucleic Acids Research*, 19, 3435–3441.

The agent for controlling apoptosis of the present invention is expected to be further applicable to various diseases accompanied with apoptosis.

The diseases accompanied with apoptosis include AIDS, neurodegenerative diseases (for instance, Alzheimer's disease, Parkinson's disease, amyotrophic lateral sclerosis, retinitis pigmentosa cerebellar degeneration and the like), osteomyelodysplastic diseases (for instance, aplastic anemia and the like), ischemic diseases (for instance, myocardial infarction, apoplexy and the like), hepatic diseases caused by intoxication with an alcohol or the like, cancers, autoimmune diseases (for instance, systemic lupus erythematosus, immune-associated glomerulonephritis and the like), viral infections (for instance, herpes viral infection, adenoviral infection and the like), diabetes, viral hepatitis and the like.

For instance, when the sense nucleic acid is used, apoptosis can be controlled positively (increase of apoptosis), so that effects for cancers, autoimmune diseases (for instance, systemic lupus erythematosus, immune-associated glomerulonephritis and the like) and viral infections (for instance, herpes viral infection, adenoviral infection and the like) are expected.

When the antisense nucleic acid or antibody is used, apoptosis can be controlled negatively (decrease of apoptosis), so that effects for AIDS, neurodegenerative diseases, osteomyelodysplastic diseases, ischemic diseases and hepatic diseases caused by intoxication with an alcohol or the like are expected.

One of the significant features of the method for controlling apoptosis of the present invention resides in the use of the above-mentioned agent for controlling apoptosis against mammals (for instance, cattle and the like). According to the method of the present invention, apoptosis can positively or negatively be controlled by selecting a peptide, a nucleic acid and an antibody to be contained in the above-mentioned agent for controlling apoptosis.

The method for controlling apoptosis of the present invention is expected to be further applicable to various diseases accompanied with apoptosis.

The present invention further provides a screening method for a substance for controlling chromatin-condensing activity.

The screening method of the present invention is concretely a screening method for a substance for controlling chromatin-condensing activity, comprising the step of evaluating an activity of causing chromatin condensation of the polypeptide of the present invention in the presence of a substance to be tested.

The activity of causing chromatin condensation can be determined in accordance with the evaluation of chromatin condensation described above.

The substance for inhibiting chromatin-condensing activity can be screened by evaluating the inhibition of an activity of causing chromatin condensation.

An expression inducer for chromatin-condensing activity can be screened by evaluating the induction of expression of an activity of causing chromatin condensation.

The enhancer for chromatin-condensing activity can be screened by evaluating the activity of causing chromatin condensation in the presence or absence of a substance to be tested.

According to the screening method of the present invention, a substance for controlling chromatin-condensing activity, such as a substance for inhibiting chromatin-condensing activity, an inducer for expressing chromatin-condensing activity or an enhancer for chromatin-condensing activity, can be screened. The substance for controlling chromatin-condensing activity is also encompassed by the present invention.

The present invention will be explained in further detail by means of the following examples, without intending to limit the present invention to the scope of the examples.

The reagents, the cells, and the like used in the following examples are given below.

Reagents Used and Cells Used

HeLa (D28/AH2) cells and Jurkat cells were grown in RPMI 1640 containing 10% fetal bovine serum. Bovine thymus glands were obtained from a slaughterhouse. Recombinant active human caspase-3 was produced and purified using the Xpress system (manufactured by Invitrogen), and was dialyzed against a transport buffer (composition: 20 mM HEPES, pH 7.3, 110 mM $CH_3COONa$, 0.5 mM EGTA, and 2 mM dithiothreitol). Recombinant human p10, human Ran, human importin $\alpha$ and importin $\beta$ were purified as described in [Imamoto, N. et al., *EMBO J.* 14, 3617–3626 (1995); Tachbana, T. et al., *FEBS Lett.* 397, 177–182 (1996); Melchior, F. et al., *Meth. Enzymol.* 257, 279–291 (1995)]. An anti-human Fas monoclonal antibody (CH-11) and an anti-Xpress antibody were obtained from MBL and Invitrogen, respectively. A polyclonal rabbit antibody against human Acinus was generated against a synthetic peptide corresponding to amino acid residues 987–1000 of AcinusL. DEVD-CHO was obtained from Osaka Peptide Institute. Hydroxyapatite was obtained from SEIKAGAKU CORPORATION, and all other column carriers used for protein purification were obtained from Pharmacia.

EXAMPLE 1

1) Preparation of Cell Lysate for In Vitro Apoptosis Assay

Jurkat cells ($4 \times 10^8$) treated with anti-Fas antibody CH-11 (0.1 $\mu$g/ml) for 3 hours and untreated cells were sonicated in 0.5 ml of lysis buffer (composition: 5 mM HEPES, pH 7.3, 10 mM $CH_3COOK$, 2 mM $(CH_3COO)_2Mg$, 5 mM $CH_3COONa$, 0.5 mM EGTA, 2 mM dithiothreitol, 10 $\mu$g/ml cytochalasin B, 50 $\mu$g/ml APMSF, and 1 $\mu$g/ml each of aprotin, leupeptin and pepstatin) and centrifuged. The resulting supernatant was concentrated with an ultrafiltration membrane-MC5,000 NMWL filter unit (manufactured by Millipore Corporation) to 20–30 mg protein/ml.

2) In vitro Apoptosis Assay with Permeabilized Cells

HeLa cells grown on plates were permeabilized as described by Adam et al. [Adam et al., *J. Cell Biol.* 111, 807–816 (1990)] with some modifications. Concretely, cells were rinsed with the transport buffer, treated with 20 $\mu$g/ml digitonin (manufactured by Wako Pure Chemicals Industries, Ltd.) for 3 minutes at room temperature, and then immersed in the transport buffer for 5 minutes. In Jurkat cells, the permeability can be improved in accordance with the method of Gorlich et al. [Gorlich et al., *Cell* 79, 767–778 (1994)]. The standard assay mixture (5 $\mu$l) was constituted by an ATP-regeneration system (composition: 1 mM ATP, 5 mM creatine phosphate, and 20 units/ml creatine phosphokinase), 1 mM GTP, 50 ng/ml of recombinant caspase-3, 0.5 mg/ml importin $\alpha$, 0.5 mg/ml importin $\beta$ 0.1 mg/ml Ran, 10 ng/ml p10, and the indicated column fractions. In the case of whole lysate (4.5 $\mu$l), only the ATP-regeneration system was added. The reaction was started by addition of the mixture to permeabilized HeLa cells on plates or to 1 $\mu$l of permeabilized Jurkat cells ($1 \times 10^6$ cells), followed by incubation at 37° C. for 2 hours. After staining with 10 $\mu$M Hoechst 33342, the nuclear changes were evaluated under a fluorescent microscope. The detection of DNA fragmentation in permeabilized Jurkat cells was carried out as described in accordance with the method by Enari et al. [Enari, M., *EMBO J.* 14, 5201–5208 (1995)].

3) Immunofluorescence Microscopy

HeLa cells grown on coverslips and permeabilized cells were fixed for 10 minutes with 3.7% formaldehyde in PBS. After treatment with 0.1% Triton X-100 in PBS for 5 minutes, the cells were incubated overnight together with 1 $\mu$g of an anti-Acinus antibody or anti-Xpress antibody in PBS containing 5% skim milk, and then were incubated with the RITC— or FITC-labeled secondary antibody.

4) Molecular Search Acting on Downstream of Caspase Capable of Responding to Nuclear Changes by Apoptosis As shown in FIG. 1, when the permeabilized HeLa cells and the lysate prepared from apoptotic Jurkat cells were incubated, apoptotic morphological changes of the nucleus, including apoptotic chromatin condensation and the like were induced in nearly all nuclei. As shown in FIG. 1, the lysate derived from live Jurkat cells treated with caspase-3 also induced similar phenomenon to the chromatin condensation in the lysate, whereas untreated lysate or caspase-3 alone did not induce any nuclear changes, thereby suggesting that the target molecule of caspase-3 responsible for chromatin condensation was present in the lysate. Further, as shown in FIG. 1, chromatin condensation was inhibited by the addition of wheat germ agglutinin, thereby suggesting the involvement of active nuclear transport.

EXAMPLE 2

Purification of Factor (Acinus) Inducing Apoptotic Chromatin Condensation from Bovine Thymus Lysate A factor inducing apoptotic chromatin condensation from bovine thymus lysate was purified in the same manner as in Example 1 described above by using this in vitro apoptosis assay.

All procedures described below were carried out at 0° to 4° C. Bovine thymus was homogenized in twice the volume of the lysis buffer. After centrifugation, the resulting supernatant was dialyzed against a buffer (20 mM Tris-HCl, pH 8.8, 2 mM $MgCl_2$, 2 mM DTT and 0.5 mM EGTA), and the resulting dialysate was applied to a HiTrap Q column (5 ml×20) equilibrated with buffer A (20 mM Tris-HCl, pH 8.5, 2 mM $MgCl_2$, 2 mM DTT, 0.5 mM EGTA, 2 mM $\beta$-glycerophosphate, and 250 mM sucrose). The column was washed with three times the volume of the column of buffer A, and proteins were eluted with 400 ml of a linear NaCl gradient (0–0.2 M). The resulting fractions of 8 ml were collected, and assayed for chromatin-condensing activity for its appropriate amount.

Since the bovine thymocytes used were partly caused to be apoptotic, inducers of apoptotic nuclear changes were expected to exist in the lysate as either proforms or active forms. Therefore, the assay was carried out in the presence of active caspase-3 in order to convert any proforms to their active forms. Components essential for active nuclear transport were supplemented to support the entry of proteins into the nucleus. After the bovine lysate was subjected to HiTrap Q column chromatography, three fractions, peaks A, B, and C, that induced chromatin condensation were detected, and peak A fraction caused typical apoptotic chromatin condensation without inducing DNA fragmentation in the oligonucleotide units. The results are shown in FIG. 2.

Figure 2:
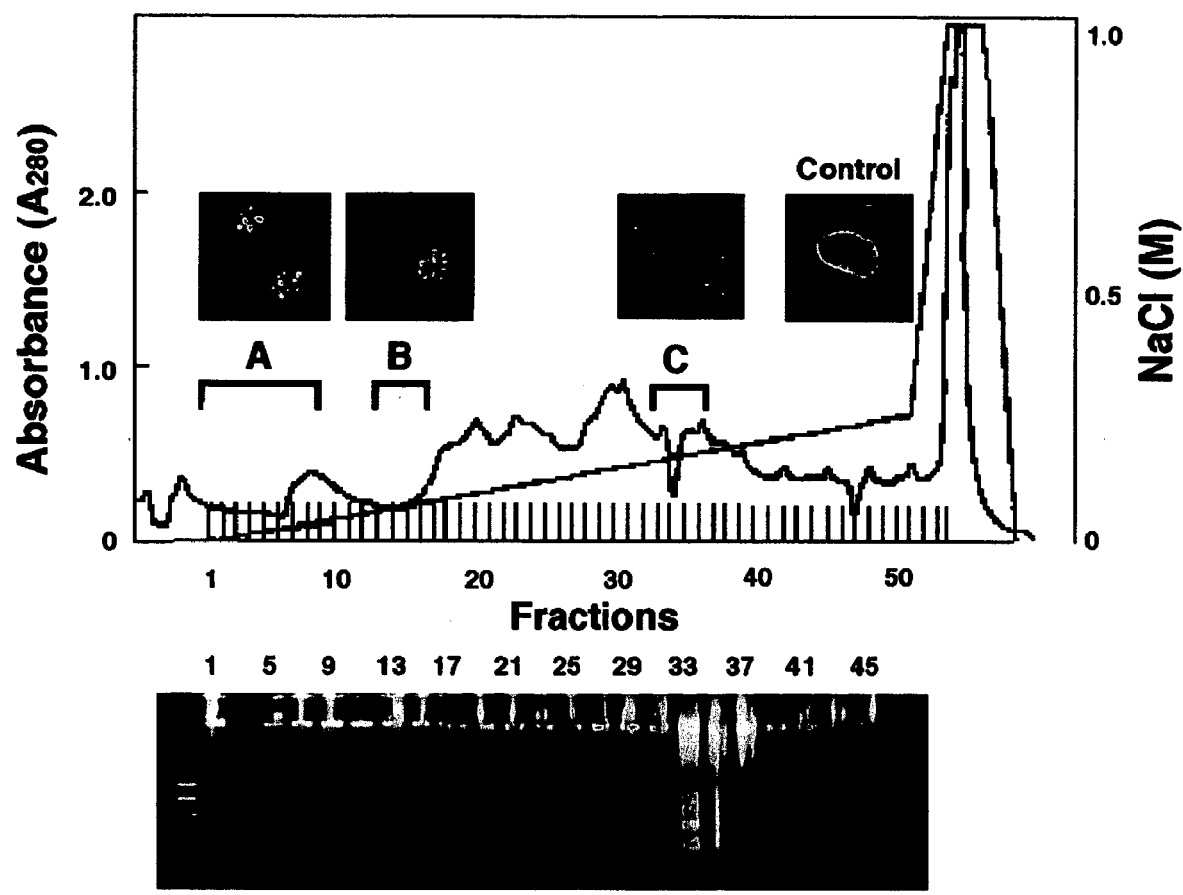
FIG. 2 is a photograph showing a profile of the separation of three distinct fractions each having an activity of inducing chromatin condensation in a bovine thymus lysate by a HiTrap Q column chromatography. Each fraction (2.5 $\mu$l) was assayed for its activity for inducing chromatin condensation using an in vitro system. Also, an upper panel of FIG. 2 shows chromatin condensation induced by each of three fractions (A, B and C). Further, a DNA ladder activity of each fraction was also assayed, and the results of an agarose gel electrophoresis are shown in a lower panel. A protein concentration was monitored by the absorbance at 280 nm.

The factor in peak B was identified as the proform of caspase-6, a protease cleaving lamin A, by microsequencing the purified protein (data not shown), and the factor in peak C was identified as a CAD/ICAD (DFF40/45)-like DNase complex that induced DNA fragmentation in the oligonucleotide units after cleavage by caspase-3 (FIG. 2).

Figure 3:
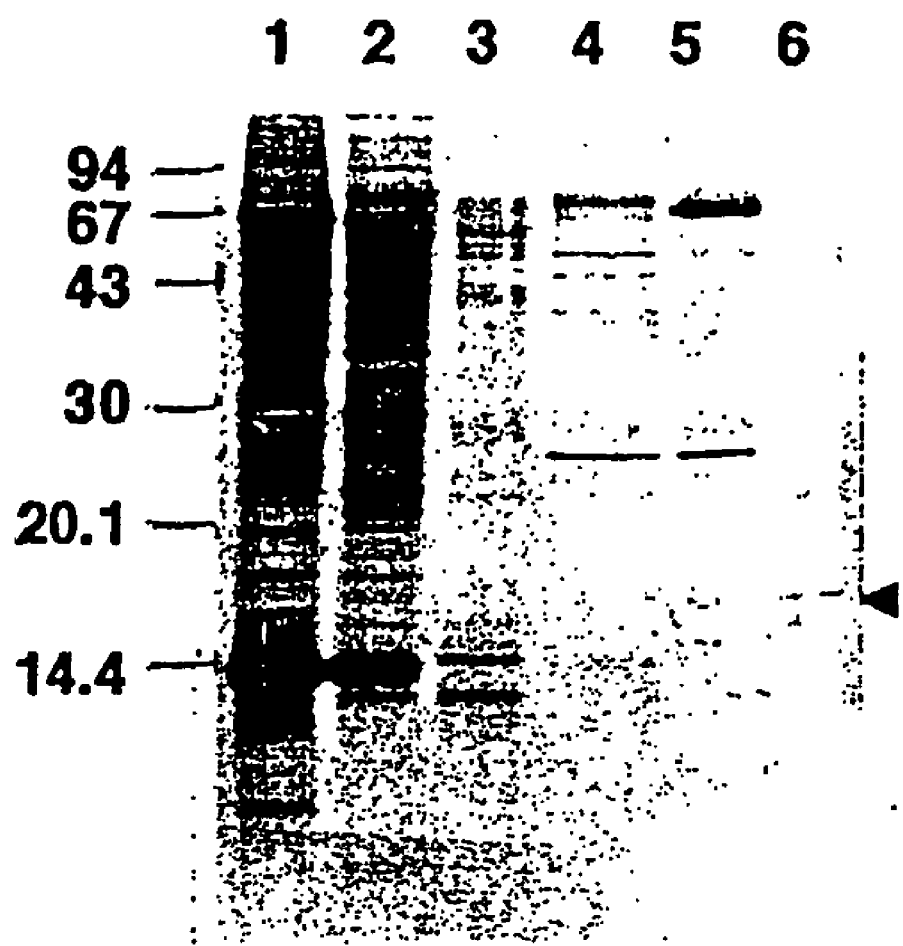
FIG. 3 shows the results obtained by subjecting an aliquot of fraction having a chromatin-condensing activity at each purification step to SDS-PAGE, and silver-staining each product. Lane 1 shows a supernatant fraction (amount of protein: 3.4 $\mu$g) centrifuged at 100000×g; Lane 2 shows a HiTrap Q fraction (amount of protein: 1.7 $\mu$g); Lane 3 shows a fraction (amount of protein: 150 ng) obtained by passing through a hydroxyapatite column, and thereafter passing through a heparin sepharose; Lane 4 shows a Phenyl-Sepharose fraction (70 ng); Lane 5 shows a Superose 12 fraction (50 ng); and Lane 6 shows a MonoQ fraction (2.5 ng). An arrowhead indicates the electrophoretic position of purified Acinus p17 protein. A molecular weight marker (kDa) is given on the left.

The Peak A fractions obtained by HiTrap Q column chromatography were passed through a hydroxyapatite column (5×10 cm) and were applied to a Heparin Sepharose column (1.5×3 cm). The column was washed with 50 ml of buffer B (composition: 20 mM Tris-HCl, pH 7.5, 2 mM $MgCl_2$, 2 mM DTT, 0.5 mM EGTA, 2 mM p-glycerophosphate, and 250 mM sucrose), and bound proteins were eluted with 10 ml of buffer B containing 1 M ammonium sulfate. The active fractions were applied to a Phenyl Sepharose column (0.8×2 cm), and the flow through fraction (10 ml) was supplemented with bovine serum albumin and concentrated to 0.5 ml. The sample was then loaded onto a Superose 12 column in buffer B. After the elution was carried out, the fractions obtained with activity were diluted ten-fold with buffer A and then applied to a Mono Q column equilibrated with buffer B. The column was washed with 20 ml of buffer A, and the elution was carried out with 30 ml of a linear NaCl concentration gradient (0–50 mM). Fractions (1 ml) were collected and stored at −80° C. Each purification step of p 17 is shown in FIG. 3 and Table 1.

TABLE 1

Purification of Acinus

| Purification Steps | Amount of Protein[a] (mg) | Entire Activity[b] (U) | Specific Activity (U/mg) | Purification Ratio (folds) | Yield (%) |
|---|---|---|---|---|---|
| 100000 × g (Supernatant) | 3680 | ND | ND | ND | ND |
| HiTrap Q | 186 | 14400 | 77.4 | 1 | 100 |
| Hydroxy-apatite/Heparin Sepharose | 2.8 | 4000 | 1428 | 18.4 | 27.8 |
| Phenyl Sepharose | 0.5 | 1680 | 3368 | 43.4 | 11.7 |
| Superose 12 | 0.1 | 1600 | 16000 | 207 | 11.1 |
| Mono Q | 0.001 | 1120 | 1120000 | 14470 | 7.78 |

[a]The amount of protein was determined by using DC protein assay kit (manufactured by BioRad), and the amount of protein of Mono Q pool was deduced by silver staining of the gel after SDS-PAGE.
[b]1 U is defined as an activity for inducing nuclear condensation in 50% of the cells. In the table, ND means that the nuclear morphologies could not be determined owing to the existence of other factor.

As a result, a protein of about 17 kDa (p17) inducing chromatin condensation was purified (FIG. 3). In addition, as shown in FIG. 4, the purified protein induced apoptotic chromatin condensation in the absence of caspase-3, suggesting that this 17 kDa protein is an active form. This factor causing the chromatin condensation was named Acinus (Apoptotic chromatin condensation inducer in the nucleus).

EXAMPLE 3

Amino Acid Sequence Analysis of Acinus

The purified protein (about 2 µg) derived from the Mono Q column obtained in the manner as described in Example 2 was subjected to 15% SDS-PAGE, and thereafter electroblotting was carried out on Immobilon membrane (manufactured by Amersham). The membrane was stained with PonceusS, and thereafter a band of a size of 17 kDa was cut out. After subjecting the band to carboxymethylation as described in Matsudaira [Matsudaira, P., Academic Press, San Diego, 1993], the modified protein was digested with 1 pmole of Acromobacter protease I, and the resulting peptides were purified using mPRC C2/C18 SC 2.1/10 with a Smart System (manufactured by Pharmacia). The sequences of the four isolated peptides were determined by a protein sequencer manufactured by Applied Biosystems (Model 470A). The results are shown in FIG. 5.

As shown by the underlined portions in FIG. 5, the four internal peptide sequences derived from the active bovine Acinus corresponded to the deduced amino acid sequences of a human KIAA clone (KIAA0670) [Ishikawa, K. et al., DNA Research 5, 196–176 (1998)] in the database. Therefore, KIAA0670 seemed to represent a human autholog of bovine acinus.

EXAMPLE 4

1) cDNA Cloning Encoding Acinus

Based on the amino acid sequences of the four peptides obtained from the purified bovine Acinus fragment of a size of 17 kDa, it was identified that the four peptides corresponded to the KIAA clone (KIAA0670) in the BLAST database. KIAA0670 DNA was a kind gift from Dr. Ohara.

As a result of screening using KLAA0670 and the like, three isoforms of human acinus cDNA (the L, S and S' forms), which were probably generated by differential splicing, were obtained. Concretely, the sequence corresponding to the 5' end of acinusL was obtained from the above-mentioned KIAA0670 by using the RACE protocol of marathon-ready cDNA. acinusS' cDNA was isolated by screening a cDNA library using PCR products corresponding to 3287–3669 bp of acinusL. acinusS cDNA was obtained by RT-PCR as a differential splicing isoform with an insertion upstream of the start codon of acinusS'. The acinus L, S, and S' cDNA contained open reading frames of 1341 amino acid residues, 583 amino acid residues, and 568 amino acid residues, respectively (see FIGS. 5 and 6).

Further, mouse acinus cDNAs were obtained by screening a library with human acinus cDNA. The mouse Acinus proteins corresponding to the human AcinusS and S' showed 94.5% and 95.2% homology of the amino acid sequences with the human AcinusS and S', respectively. A protein database (BLAST) search revealed that Acinus derived from human or mouse contained a region resembling the RNA recognition motif of Drosophila Sx1. The results are shown in FIG. 7. Only AcinusL had a P-loop for nucleotide binding near the N-terminus.

2) Preparation of Acinus Recombinant Protein (rAcinus)

Full length rAcinusS and rAcinusΔN were produced as a GST fusion protein and a His$_6$-tagged protein, respectively.

Concretely, acinusS cDNA was subcloned into pGEX1T (manufactured by Pharmacia), and thereafter *E. coli* DHa strain was transfected by using the resulting plasmid. Protein production was induced by the addition of IPTG (final concentration: 0.1 mM). Bacteria were incubated at 20° C. overnight and lysed in the same lysis buffer as that used for the protein derived from bovine thymus. GST-AcinusS was purified with Glutathione Sepharose CL-4B (Pharmacia) according to the protocol of the manufacturer. The purity was estimated to be about 90% by CBB staining.

acinusΔN and acinusΔN (D/A) (one resulting from substitution of 1093rd aspartic acid with alanine) cDNA were subcloned into pREST (manufactured by Invitrogen). Expression of the protein was induced by infection with M13 phage for producing T7 polymerase (M13-KM2), and His-tagged Acinus proteins were purified on nickel affinity column (manufactured by Novagen).

rAcinus (987–1093) was prepared by cleavage of rAcinusΔN with caspase-3 and was purified by HiTrap Q column chromatography. Since the purity of the His-tagged proteins was not high (purity of about 10%), the amount of the protein was estimated from the concentration visualized by immunoblotting.

Figure 8:
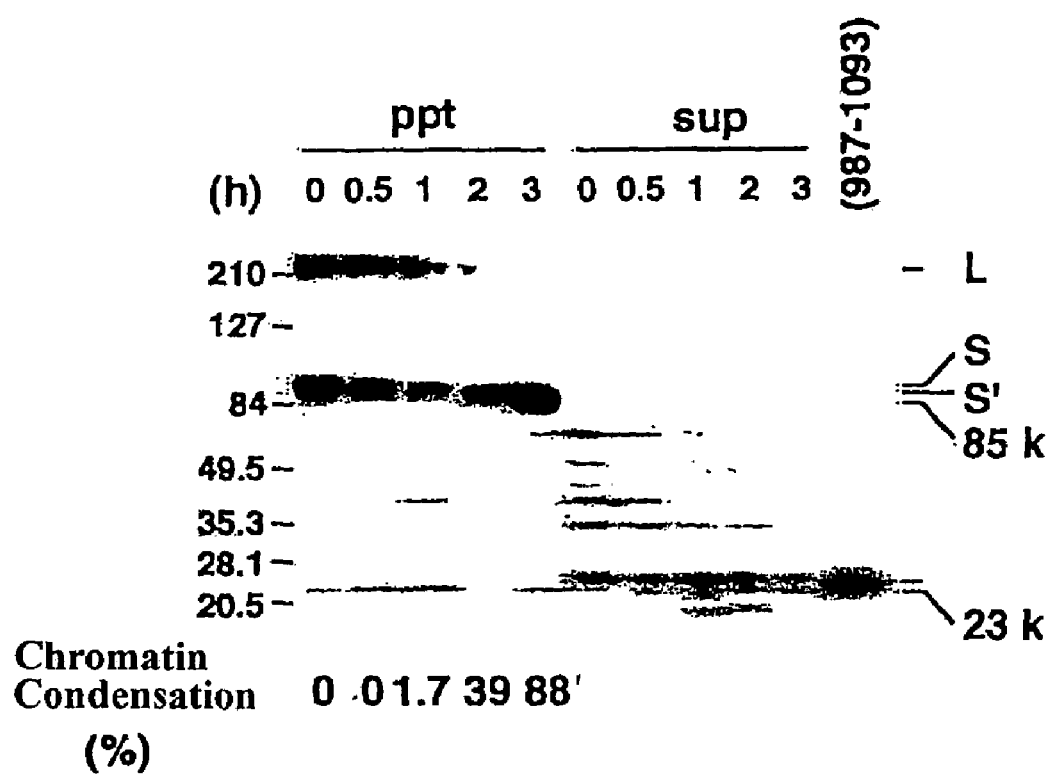
FIG. 8 shows the results of an in vivo cleavage of Acinus in Fas-mediated apoptosis. Jurkats cells were treated with 0.1 $\mu$g/ml anti-Fas antibody for an indicated time period (hours), and lyzed with a lysis buffer containing 1% Triton X-100. After centrifugation, the supernatant and a pellet were dissolved in SDS sample buffer to be subjected to SDS-PAGE. rAcinus resulting from removing His-tag by an enterokinase treatment of His-tagged Acinus (987–1093) expressed by using a vector (manufactured by NOVAGEN) employed for producing His-tagged protein was also subjected to SDS-PAGE at the same time. After SDS-PAGE, a protein band was transferred onto a membrane, and analyzed with an anti-Acinus antibody. The positions of the AcinusL, S, S' and the cleaved fragments (85 kDa and 23 kDa) are indicated. The ratio (%) of the cells showing apoptotic chromatin condensation after nuclear treatment time is indicated in a lower column of the figure showing the electrophoretic results.

The apparent molecular weights of AcinusL, S, and S' on SDS-polyacrylamide gel were about 220 kDa, about 98 kDa and about 94 kDa, respectively (data not shown). The human AcinusL, S, and S' along with low-molecular weight Acinus were present in Jurkat cells (FIG. 8). The majority of the three forms of the human Acinus was recovered in a TritonX-100-insobuble fraction, while most of the low-molecular weight Acinus was a soluble fraction (FIG. 8). The nature of low-molecular weight Acinus was not determined, and they might have been in proteolytically processed forms or unidentified isoforms of Acinus. During Fas-mediated apoptosis, as shown in FIG. 8, AcinusL, S, and S' as well as some of the low-molecular weight Acinus were reduced before chromatin condensation became evident, while an 85 kDa protein in the insoluble fraction and a 23 kDa protein in the soluble fraction newly emerged accompanying chromatin condensation. This suggests that Acinus was cleaved by the caspase, generating active fragments.

EXAMPLE 5

Identification of Active Form of Human Acinus

Purified active bovine Acinus p17 seemed to be subjected to truncation at both N- and C-terminal sites, on the bases that (1) N-terminal sequence analysis revealed that p17 started as Ser$^{987}$, and (2) the size of p17 indicated C-terminal truncation. A plural forms of recombinant Acinus (hereinafter referred to as "rAcinus"): AcinusS, ΔN (from Ser$^{987}$ to the C-terminus), ΔN (D/A), and Acinus (987–1093) (from Ser$^{987}$ to Asp$^{1093}$) were prepared, and their chromatin-condensing activity, cleavage by caspase-3, and the role of N-terminal site in activation of Acinus were studied.

As shown in FIG. 9, human AcinusS was actually cleaved with caspase-3 in vivo, and the cleavage site was determined to be the Asp$^{1093}$ of DELD$^{1093}$ by microsequencing of the cleavage product of recombinant AcinusS. This result was identical to the consensus DxxD target sequence for caspase-3. Consistently, a mutation of substituting Asp$^{1093}$ with Ala (D/A) abolished the in vitro cleavage of Acinus by caspase-3.

Figure 10:
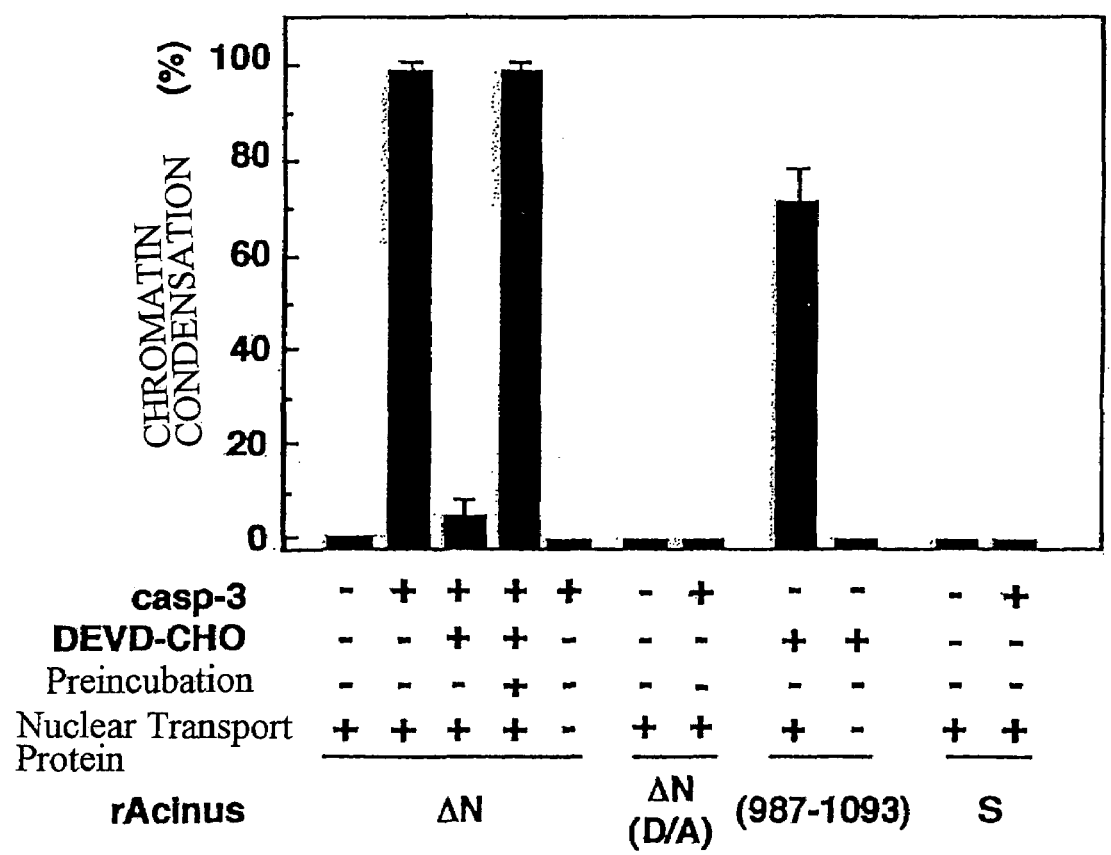
FIG. 10 is a graph showing the results of chromatin condensation induction by a recombinant Acinus in permeabilized cells. The induction by rAcinus of the chromatin condensation is dependent on caspase-3 and nuclear transport. Each of rAcinus$\Delta$N (about 0.05 $\mu$g), rAcinus$\Delta$N (D/A) (about 0.06 $\mu$g), rAcinus (987–1093) (0.1 $\mu$g) and rAcinusS (0.1 $\mu$g) was added to cells permeabilized in the presence or absence of caspase-3, DEVD-CHO and a nuclear transport protein as shown in the figure, and the mixture was incubated for 2 hours. rAcinus$\Delta$N was preincubated with caspase-3 at 37° C. for 1 hour. After staining with Hoechst 33324, the chromatin condensation was evaluated with a fluorescent microscope. The data are shown as means±s.d (n=4).

In addition, as shown in FIG. 10, rAcinusΔN exhibited chromatin-condensing activity in the presence of caspase-3, but did not exhibit chromatin-condensing activity in the presence of a caspase-3 inhibitor DEVD-CHO or in the absence of caspase-3, and at the same time rAcinusΔN with Asp$^{1093}$/Ala (D/A) mutation [ΔN(D/A)] did not induce chromatin condensation in the presence of caspase-3. These results indicated that cleavage of rAcinusΔN by caspase-3 at Asp$^{1093}$ was essential for the chromatin-condensing activity.

In addition, as shown in FIG. 10, rAcinusΔN preincubated with caspase-3 induced chromatin condensation even in the presence of DEVD-CHO, indicating that caspase-3 activity was no longer required for chromatin condensation after cleavage of Acinus. Supporting this fact, rAcinus (987–1093) induced chromatin condensation in the absence of caspase-3 and in the presence of DEVD-CHO, similarly to bovine Acinus p17.

Further, as shown in FIG. 10, although the possibility that rAcinusS was not properly folded was not excluded, since full length rAcinusS had no chromatin-condensing activity, it is seen that cleavage at Ser$^{987}$ of the full length rAcinusS was also necessary for chromatin activity. The results for the observation (FIG. 8) that apoptotic Jurkat cells contained a 23 kDa protein with a size corresponding to rAcinus (987–1093) in a newly emerging Acinus fragment indicated that Acinus (987–1093) was one of the active forms of Acinus which induced chromatin condensation. Therefore, it is evident that the active form of bovine Acinus p17 corresponded to Acinus (987–1093), and the size difference between human and bovine active Acinus might have been due to some amino acid changes or further truncation at the C-terminus of bovine Acinus.

Figure 11:
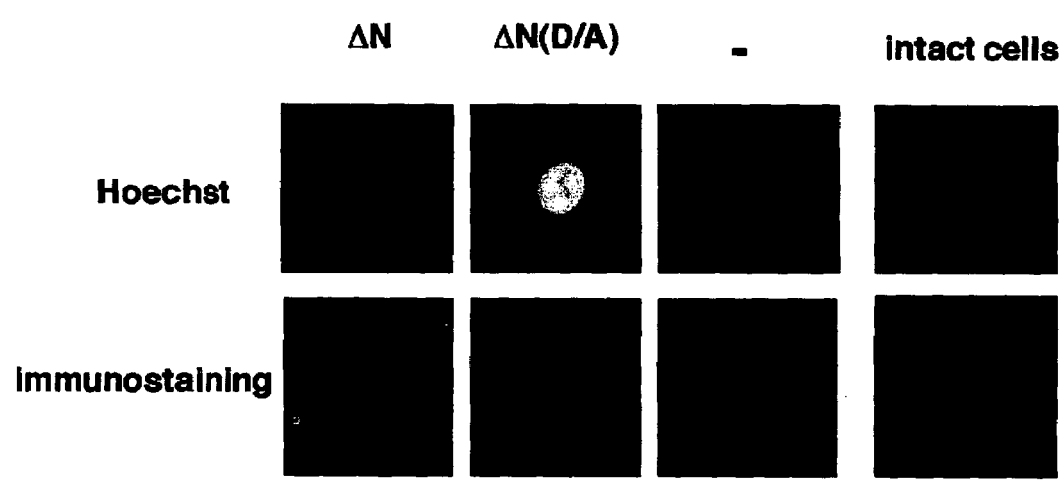
FIG. 11 is a photograph showing the nuclear localization of Acinus in permeabilized cells, and in intact cells. Permeabilized HeLa cells were incubated with each of His-tagged rAcinusΔN and ΔN (D/A) and then immunostained with each of an anti-Xpress antibody and an FITC-labelled secondary antibody. The intact HeLa cells were immunostained with an anti-Acinus antibody and then an RITC-labelled secondary antibody. Further, the nucleus was visualized by means of Hoechst 33342 staining. Each photomicrograph is obtained from an identical field of vision.

Active nuclear transport proteins were required for the induction of chromatin condensation by rAcinus (FIG. 10), suggesting that nuclear localization of Acinus was essential for its chromatin-condensing activity in the in vitro apoptosis assay system. In fact, a significant amount of rAcinusΔN was translocated to the nucleus in vitro as shown by immunostaining of permeabilized cells. In addition, as shown in FIG. 11, since rAcinusΔN (D/A) was also transported to the nucleus, cleavage of Acinus by caspase was not essential for nuclear localization. As shown in FIG. 11, endogenous Acinus was mainly detected in the nucleus, suggesting a possibility that the caspase is transported into the nucleus to proteolytically activate Acinus during in vivo apoptosis. Alternatively, the chromatin condensation is thought to be induced after a small amount of Acinus or proteolytically processed Acinus may be present in the cytoplasm, cleaved by the caspase and transported to the nucleus. Localization of the endogenous Acinus in discrete areas of the nucleus suggested its association with a certain kind of a nuclear structure.

Figure 12:
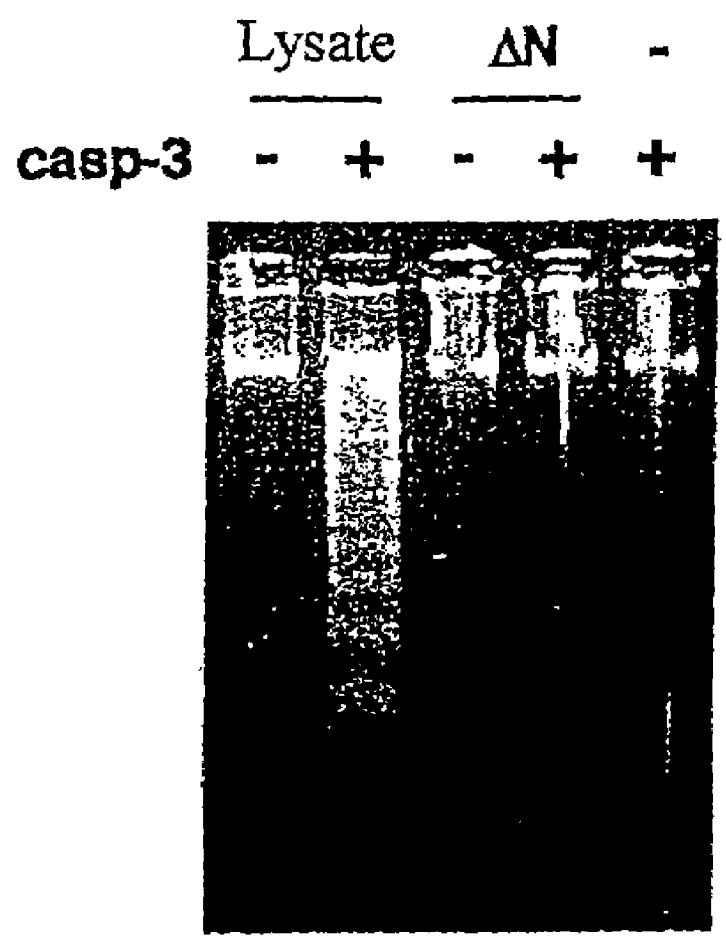
FIG. 12 shows the results obtained by incubating permeabilized Jurkat cells, in the presence or absence of caspase-3 together with a normal Jurkat cell lysate or rAcinusΔN for 2 hours, and subjecting the nuclear DNA to electrophoresis on agarose gel.

Consistent with the observation that purified bovine Acinus caused chromatin condensation without oligonucleosomal DNA fragmentation, as shown in FIG. 12, no DNA fragmentation was observed when rAcinus induced chromatin condensation in vitro. Therefore, it is suggested that Acinus produces apoptotic chromatin condensation by a mechanism independent of DNA fragmentation in the oligonucleotide units.

EXAMPLE 6

Influence of Immunodepletion of Acinus

In order to determine whether or not Acinus was essential for apoptotic chromatin condensation, the ability of inducing chromatin condensation in vitro of normal Jurkat cell lysate and apoptotic Jurkat cell lysate each immunodepleted of Acinus was tested. Jurkat cell lysate was prepared as described above. Antibody-loaded protein G-beads were prepared as described in Hirano et al. [Hirano, T. et al., *Cell* 89, 511–521 (1997)]. For immunodepletion of Acinus, lysates were incubated with an equal volume of the above beads at 4° C. for 2 hours with rotation. The supernatants were recovered by two rounds of brief spinning to be used as immunodepleted lysates.

Figure 13:
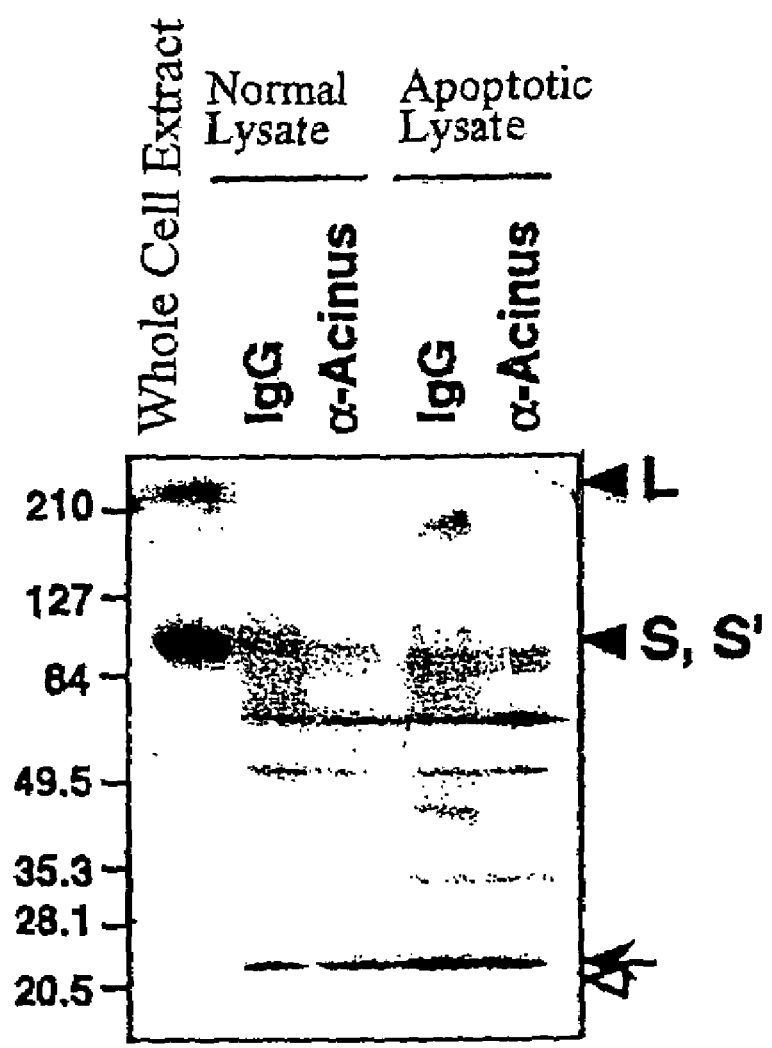
FIG. 13 shows the results of immunodepletion of Acinus derived from a Jurkat cell lysate. Each of the untreated Jurkat cell lysate (indicated by "normal lysate" in the figure) and the Jurkat cell lysate treated with an anti-Fas antibody for three hours (indicated by "apoptosis lysate" in the figure) were incubated with a control IgG antibody- or an anti-Acinus antibody-conjugated protein G sepharose. A treated lysate was separated by SDS-PAGE and immunoblotted with an anti-Acinus antibody. Further, a whole cell extract from normal Jurkat cells dissolved in an SDS sample buffer was loaded onto the leftmost lane for the purpose of identifying the band of endogenous Acinus. Each arrowhead indicates the band of the AcinusL, S, S' and Acinus (987–1093). An arrow indicates one of the unidentified proteins different from Acinus (987–1093).
Figure 14:
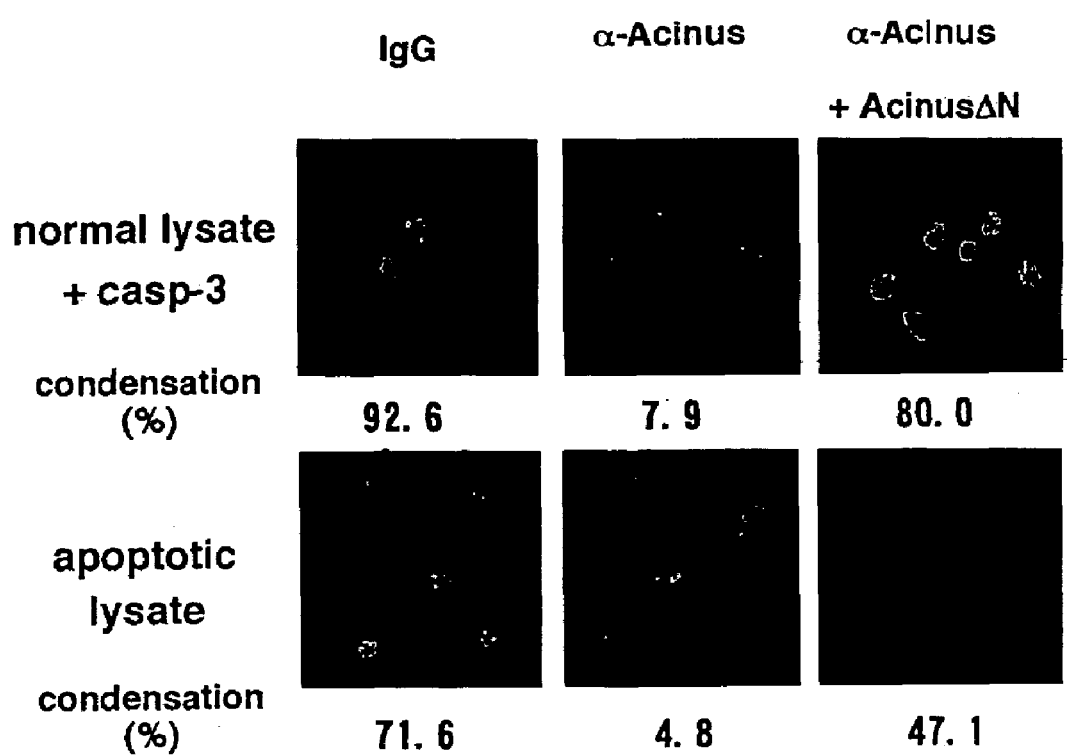
FIG. 14 is a photograph showing that Acinus-immunodepletion lysate does not induce chromatin condensation and recovers its activity by rAcinusΔN. An immunodepleted lysate (5 μl) derived from live cells (indicated by "normal lysate" in the figure) immunodepleted by an indicated antibody was added together with or without the rAcinusΔN (0.5 μg) to permeabilized cells in the presence of caspase-3. An immunodepleted lysate derived from an anti-Fas antibody-treated cell (indicated by "apoptosis lysate" in the figure) was added in the absence of caspase-3. The nucleus was visualized by means of Hoechst 33342 staining. The ratio (%) of the nucleus exhibiting chromatin condensation is indicated under each fluorescent photomicrograph.

The reduction in the amount of Acinus in the normal cell lysate and the apoptotic cell lysate was confirmed by immunoblotting (FIG. 13), whereas CAD/DFF40 activity as evaluated with the permeabilized cells remained unchanged. Although it is seen that the immunoblot profile shown in FIG. 13 is slightly different from one in FIG. 8, it is probably due to a much larger number of cells used to prepare the lysates in FIG. 13. As shown in FIG. 14, lysates immunodepleted with anti-Acinus antibody did not induce chromatin condensation. Addition of rAcinusΔN restored the chromatin-condensing activity of the immunodepleted lysates. Also, the lysate treated with a control antibody showed chromatin-condensing activity. These results indicated that Acinus was indispensable for apoptotic chromatin condensation in the in vitro system. The lysates immunodepleted with the anti-Acinus antibody, as shown in FIG. 14, caused slight accumulation of chromatin at the nuclear periphery and slight nuclear shrinkage, which may have been due to the incomplete immunodepletion of Acinus or due to the presence of other factors causing nuclear changes, including caspase-6 and CAD/DFF40.

EXAMPLE 7

Transfection and Analysis of Nuclear Changes

The role of Acinus in the in vivo apoptotic process was examined by transient transfection of sense or antisense acinusL cDNA into HeLa cells.

acinusL, S, S', and S'(D/A) cDNAs were cloned in the pCAGGS vector [Niwa, H. et al., *Gene* 108, 193–199 (1991)]. Further, acinusL cDNA was cloned in the vector in an opposite orientation [acinusL(R)]. acinus cDNA (1 μg) was transfected into 0.5×10⁶ HeLa or COS-7 cells together with 0.1 μg of pEGFP-C1 (manufactured by Clontech) using Lipofectamine (manufactured by Gibco). Cells were incubated for 48 hours in medium supplemented with 10% fetal bovine serum. For immunoblotting, cells were lysed with SDS sample buffer and subjected to SDS-PAGE. Cell death was induced by the addition of 100 μM etoposide. After the indicated period, cells were stained with Hoechst 33342. Subsequently, the GFP-positive apoptotic cells and live cells were counted.

Figure 15:
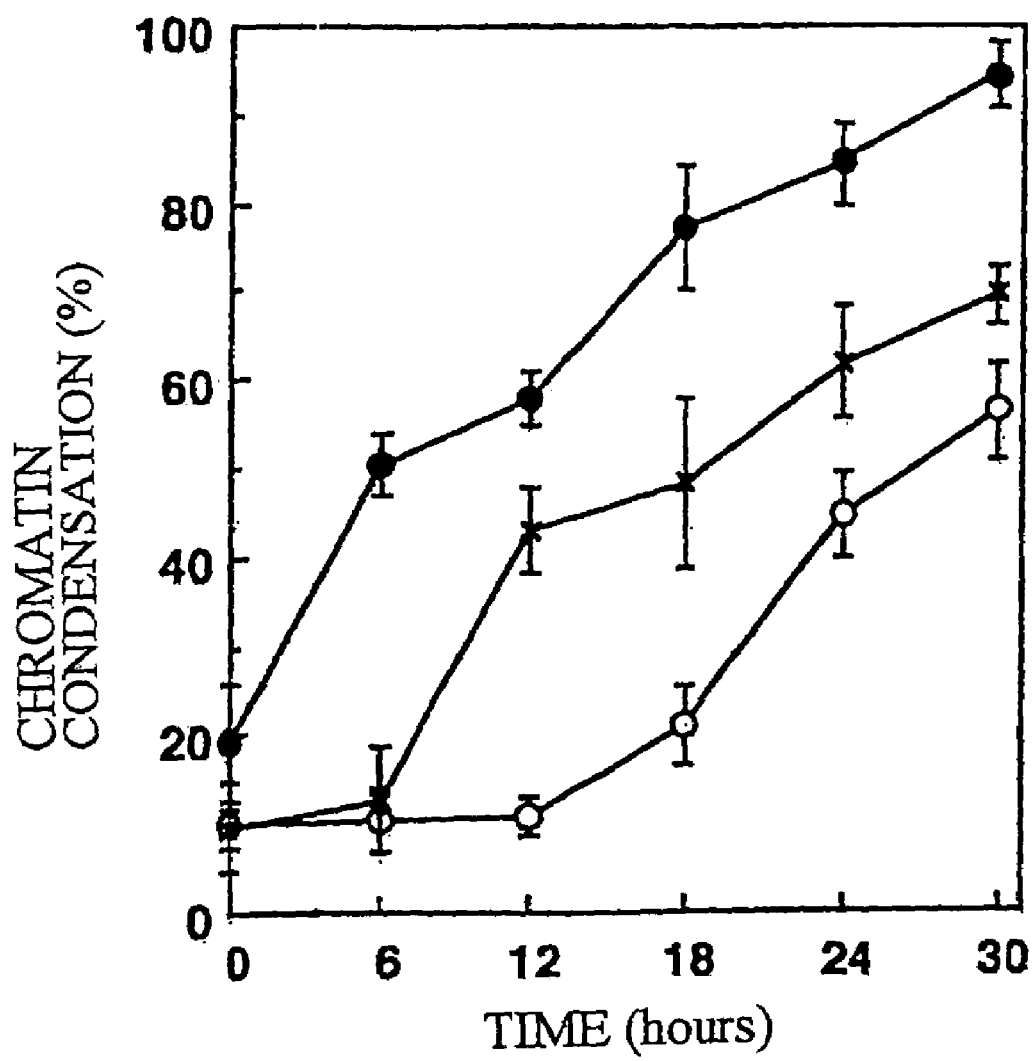
FIG. 15 shows the enhancement and the retardation of chromatin condensation in HeLa cells transfected with acinusL plasmid in the sense direction and the antisense direction. 1 μg of pCAGGS-acinusL (sense: indicated by solid circles in the figure), pCAGGS-acinusL (R) (antisense: indicated by open circles in the figure) or a vector (indicated by x in the figure) was transfected into HeLa cells together with a GFP-expressing plasmid (0.1 μg). After 48 hours, the cells were further incubated for an indicated time period in the presence of 100 μM etoposide. The chromatin condensation in GFP-positive cells was evaluated by means of Hoechst 33342 staining. The results are shown as means±s.d (n=4).
Figure 16:
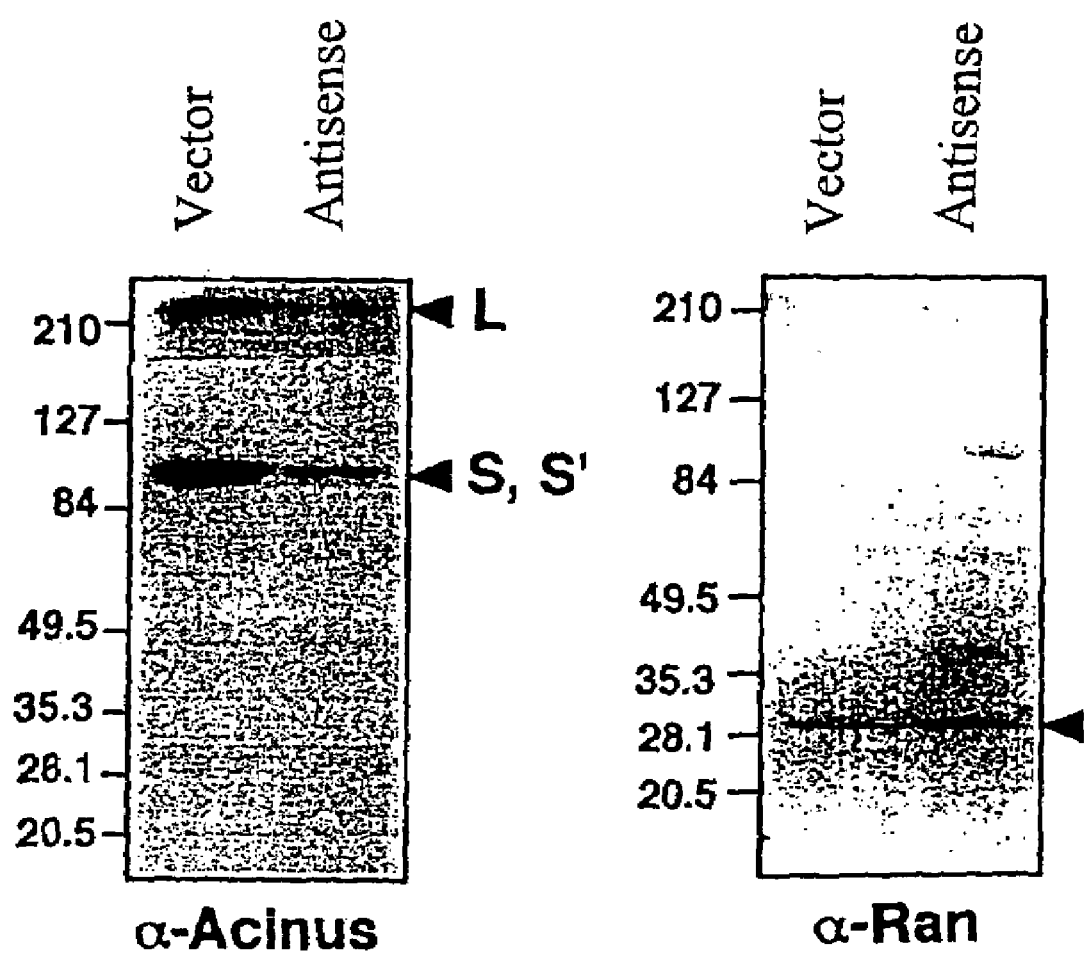
FIG. 16 shows the reduction in endogenous Acinus by the transfection with acinusL (R) antisense plasmid. HeLa cells (0.5×10⁶) were transfected with 1 μg of a pCAGGS-acinusL (R) plasmid or only with a vector. After 48 hours, the cells were harvested, and the whole cell extract was prepared by use of an SDS sample buffer. A sample was subjected to SDS-PAGE, and then immunoblotted with an anti-Acinus antibody (left panel) and an anti-Ran antibody (right panel). The AcinusL, S, S' and Ran were indicated by arrowheads.

A GFP marker plasmid was co-transfected to identify the DNA-transfected cells. The sense plasmid caused slight induction of chromatin condensation without any apoptotic stimuli, and enhanced apoptotic chromatin condensation induced by etoposide, topoisomerase II inhibitor (FIG. 15). Conversely, in the antisense plasmid, chromatin condensation induced by etoposide was effectively delayed (FIG. 15). After transfection with the antisense acinus plasmid, down-regulation specific to endogenous Acinus was verified by immunoblotting (FIG. 16). Further, expression of Acinus (987–1093) in HeLa cells, which was active in inducing chromatin condensation in vitro, was also tried, but its expression was undetectable, probably due to instability in vivo. These results suggested that Acinus further played a significant role in apoptotic chromatin condensation in vivo.

It has been reported that CAD/DFF40 can induce chromatin condensation in isolated nuclei, and that in thymocytes and splenocytes being deficient of DFF40 (consequently being deficient of functional DFF40), apoptotic chromatin condensation is impaired, suggesting that CAD/DFF40 is involved in chromatin condensation. However, there may be other factors required for apoptotic chromatin condensation, because (1) apoptotic chromatin condensation is not completely abolished in DFF40-deficient cells, (2) ICAD (an inhibitor of CAD/DFF40) does not inhibit chromatin condensation is isolated nuclei induced by apoptotic cell lysates, and (3) CAD is not expressed in human tissues and cell lines where apoptotic chromatin condensation is observed. Since Acinus is ubiquitously expressed, Acinus is likely to play an important role in apoptotic chromatin condensation in general, even though CAD/DFF40 might play a dominant role in inducing chromatin condensation in certain cells. It is also possible that Acinus-induced chromatin condensation is facilitated by CAD/DFF40.

Acinus is essential for apoptotic chromatin condensation, and it might also be involved in nuclear structural changes occurring in normal cells, such as chromatin condensation in the M-phase and nuclear mitosis. Acinus has a P-loop motif and a region similar to the RNA recognition motif of Sx1, suggesting that Acinus might possess ATPase activity and DNA/RNA binding activity. Further studies on Acinus are considered to serve to elucidate not only the process of apoptotic nuclear changes but also nuclear functions in viable cells.

Sequence Listing Free Text

In SEQ ID NO: 5, n in the base number: 1 means that an exact sequence could not be determined because the signals overlapped.

In SEQ ID NO: 6, each of n in the base numbers: 20, 104, 114, 148 and 156 means that an exact sequence could not be determined because the signals overlapped.

INDUSTRIAL APPLICABILITY

According to the polypeptide, the nucleic acid, and the antibody of the present invention, there can be exhibited excellent effects such that the polypeptide, the nucleic acid, and the antibody can be utilized for searches for a factor for which the polypeptide is used as a target molecule in control of apoptosis, searches for a molecule for which the polypeptide is targeted, and the like, and further that they can be effectively used for controlling apoptosis. In addition, according to the agent for controlling apoptosis and the method of controlling apoptosis, the apoptosis can be positively or negatively controlled. In the agent for controlling apoptosis and the method of controlling apoptosis mentioned above, their applications to various diseases accompanying apoptosis are expected.

The invention claimed is:

1. A polypeptide possessing an action of causing in vitro chromatin condensation in the presence of caspase-3, consisting of a sequence selected from the group consisting of:
   (A) the amino acid sequence of SEQ ID NO:4; and
   (B) an amino acid sequence encoded by a nucleic acid consisting of 321 nucleotides that hybridizes to the complete complement of SEQ ID NO:8, wherein said hybridizing occurs at 42° C. in a solution containing 6×SSC, 0.5% SDS and 50% formamide solution, with washing thereafter at 68° C. in a solution containing 0.1×SSC and 0.5% SDS, wherein said amino acid encoded by the nucleic acid possesses an action of causing in vitro chromatin condensation in the presence of caspase-3.

2. The polypeptide according to claim 1, wherein the polypeptide possesses an action of causing in vitro chromatin condensation without accompanying DNA fragmentation.

3. An agent for causing in vitro chromatin condensation, comprising the polypeptide of claim 1 or 2.

4. A screening method for a test substance for controlling chromatin-condensing activity in the presence of caspase-3, comprising
   (a) incubating the test substance with permeabilized cells in the presence of the polypeptide of claim 1 or 2; and
   (b) evaluating an activity of causing chromatin condensation exhibited by the polypeptide.

5. A screening method for a test substance for controlling chromatin-condensing activity in the presence of caspase-3, comprising
   (a) incubating the test substance with permeabilized cells in the presence of the polypeptide of claim 1 or 2; and
   (b) evaluating an activity of inhibiting chromatin condensation exhibited by the polypeptide.

6. The screening method according to claim 4, wherein said activity is enhancing chromatin condensation.

7. The polypeptide according to claim 1, wherein said polypeptide is encoded by a nucleic acid consisting of the nucleotide sequence of SEQ ID NO: 8.

8. A polypeptide for causing in vitro chromatin condensation, consisting of the polypeptide of claim 1 or 2.

* * * * *

SEQUENCE LISTING

<160> NUMBER OF SEQ ID NOS: 11

<210> SEQ ID NO 1
<211> LENGTH: 1341
<212> TYPE: PRT
<213> ORGANISM: Homo sapiens

<400> SEQUENCE: 1

```
Met Trp Arg Arg Lys His Pro Arg Thr Ser Gly Gly Thr Arg Gly Val
 1               5                  10                  15

Leu Ser Gly Asn Arg Gly Val Glu Tyr Gly Ser Gly Arg Gly His Leu
            20                  25                  30

Gly Thr Phe Glu Gly Arg Trp Arg Lys Leu Pro Lys Met Pro Glu Ala
        35                  40                  45

Val Gly Thr Asp Pro Ser Thr Ser Arg Lys Met Ala Glu Leu Glu Glu
    50                  55                  60

Val Thr Leu Asp Gly Lys Pro Leu Gln Ala Leu Arg Val Thr Asp Leu
 65                  70                  75                  80

Lys Ala Ala Leu Glu Gln Arg Gly Leu Ala Lys Ser Gly Gln Lys Ser
                85                  90                  95

Ala Leu Val Lys Arg Leu Lys Gly Ala Leu Met Leu Glu Asn Leu Gln
            100                 105                 110

Lys His Ser Thr Pro His Ala Ala Phe Gln Pro Asn Ser Gln Ile Gly
        115                 120                 125

Glu Glu Met Ser Gln Asn Ser Phe Ile Lys Gln Tyr Leu Glu Lys Gln
    130                 135                 140

Gln Glu Leu Leu Arg Gln Arg Leu Glu Arg Glu Ala Arg Glu Ala Ala
145                 150                 155                 160

Glu Leu Glu Glu Ala Ser Ala Glu Ser Glu Asp Glu Met Ile His Pro
                165                 170                 175

Glu Gly Val Ala Ser Leu Leu Pro Pro Asp Phe Gln Ser Ser Leu Glu
            180                 185                 190

Arg Pro Glu Leu Glu Leu Ser Arg His Ser Pro Arg Lys Ser Ser Ser
        195                 200                 205

Ile Ser Glu Glu Lys Gly Asp Ser Asp Glu Lys Pro Arg Lys Gly
    210                 215                 220

Glu Arg Arg Ser Ser Arg Val Arg Gln Ala Arg Ala Lys Leu Ser
225                 230                 235                 240

Glu Gly Ser Gln Pro Ala Glu Glu Glu Asp Gln Glu Thr Pro Ser
                245                 250                 255

Arg Asn Leu Arg Val Arg Ala Asp Arg Asn Leu Lys Thr Glu Glu Glu
            260                 265                 270

Glu Glu Glu Glu Glu Glu Glu Glu Asp Asp Glu Glu Glu Gly
        275                 280                 285

Asp Asp Glu Gly Gln Lys Ser Arg Glu Ala Pro Ile Leu Lys Glu Phe
    290                 295                 300

Lys Glu Glu Gly Glu Ile Pro Arg Val Lys Pro Glu Glu Met Met
305                 310                 315                 320

Asp Glu Arg Pro Lys Thr Arg Ser Gln Glu Gln Glu Val Leu Glu Arg
                325                 330                 335

Gly Gly Arg Phe Thr Arg Ser Gln Glu Glu Ala Arg Lys Ser His Leu
            340                 345                 350

Ala Arg Gln Gln Gln Glu Lys Glu Met Lys Thr Thr Ser Pro Leu Glu
```

-continued

```
                355                 360                 365
Glu Glu Glu Arg Glu Ile Lys Ser Ser Gln Gly Leu Lys Glu Lys Ser
        370                 375                 380

Lys Ser Pro Ser Pro Pro Arg Leu Thr Glu Asp Arg Lys Lys Ala Ser
385                 390                 395                 400

Leu Val Ala Leu Pro Glu Gln Thr Ala Ser Glu Glu Thr Pro Pro
                405                 410                 415

Pro Leu Leu Thr Lys Glu Ala Ser Ser Pro Pro His Pro Gln Leu
                420                 425                 430

His Ser Glu Glu Glu Ile Glu Pro Met Glu Gly Pro Ala Pro Val
        435                 440                 445

Leu Ile Gln Leu Ser Pro Pro Asn Thr Asp Ala Asp Thr Arg Glu Leu
        450                 455                 460

Leu Val Ser Gln His Thr Val Gln Leu Val Gly Gly Leu Ser Pro Leu
465                 470                 475                 480

Ser Ser Pro Ser Asp Thr Lys Ala Glu Ser Pro Ala Glu Lys Val Pro
                485                 490                 495

Glu Glu Ser Val Leu Pro Leu Val Gln Lys Ser Thr Leu Ala Asp Tyr
                500                 505                 510

Ser Ala Gln Lys Asp Leu Glu Pro Glu Ser Asp Arg Ser Ala Gln Pro
        515                 520                 525

Leu Pro Leu Lys Ile Glu Glu Leu Ala Leu Ala Lys Gly Ile Thr Glu
        530                 535                 540

Glu Cys Leu Lys Gln Pro Ser Leu Glu Gln Lys Glu Gly Arg Arg Ala
545                 550                 555                 560

Ser His Thr Leu Leu Pro Ser His Arg Leu Lys Gln Ser Ala Asp Ser
                565                 570                 575

Ser Ser Ser Arg Ser Ser Ser Ser Ser Ser Ser Ser Arg Ser Arg
                580                 585                 590

Ser Arg Ser Pro Asp Ser Ser Gly Ser Arg Ser His Ser Pro Leu Arg
        595                 600                 605

Ser Lys Gln Arg Asp Val Ala Gln Ala Arg Thr His Ala Asn Pro Arg
        610                 615                 620

Gly Arg Pro Lys Met Gly Ser Arg Ser Thr Ser Glu Ser Arg Ser Arg
625                 630                 635                 640

Ser Arg Ser Arg Ser Arg Ser Ala Ser Asn Ser Arg Lys Ser Leu
                645                 650                 655

Ser Pro Gly Val Ser Arg Asp Ser Ser Thr Ser Tyr Thr Glu Thr Lys
                660                 665                 670

Asp Pro Ser Ser Gly Gln Glu Val Ala Thr Pro Val Pro Gln Leu
                675                 680                 685

Gln Val Cys Glu Pro Lys Glu Arg Thr Ser Thr Ser Ser Ser Ser Val
        690                 695                 700

Gln Ala Arg Arg Leu Ser Gln Pro Glu Ser Ala Glu Lys His Val Thr
705                 710                 715                 720

Gln Arg Leu Gln Pro Glu Arg Gly Ser Pro Lys Lys Cys Glu Ala Glu
                725                 730                 735

Glu Ala Glu Pro Pro Ala Ala Thr Gln Pro Gln Thr Ser Glu Thr Gln
                740                 745                 750

Thr Ser His Leu Pro Glu Ser Glu Arg Ile His His Thr Val Glu Glu
        755                 760                 765

Lys Glu Glu Val Thr Met Asp Thr Ser Glu Asn Arg Pro Glu Asn Asp
770                 775                 780
```

```
Val Pro Glu Pro Pro Met Pro Ile Ala Asp Gln Val Ser Asn Asp Asp
785                 790                 795                 800

Arg Pro Glu Gly Ser Val Glu Asp Glu Glu Lys Lys Glu Ser Ser Leu
            805                 810                 815

Pro Lys Ser Phe Lys Arg Lys Ile Ser Val Val Ser Ala Thr Lys Gly
            820                 825                 830

Val Pro Ala Gly Asn Ser Asp Thr Glu Gly Gln Pro Gly Arg Lys
            835                 840                 845

Arg Arg Trp Gly Ala Ser Thr Ala Thr Thr Gln Lys Lys Pro Ser Ile
850                 855                 860

Ser Ile Thr Thr Glu Ser Leu Lys Ser Leu Ile Pro Asp Ile Lys Pro
865                 870                 875                 880

Leu Ala Gly Gln Glu Ala Val Val Asp Leu His Ala Asp Ser Arg
            885                 890                 895

Ile Ser Glu Asp Glu Thr Glu Arg Asn Gly Asp Asp Gly Thr His Asp
            900                 905                 910

Lys Gly Leu Lys Ile Cys Arg Thr Val Thr Gln Val Val Pro Ala Glu
            915                 920                 925

Gly Gln Glu Asn Gly Gln Arg Glu Glu Glu Glu Glu Lys Glu Pro
930                 935                 940

Glu Ala Glu Pro Pro Val Pro Pro Gln Val Ser Val Glu Val Ala Leu
945                 950                 955                 960

Pro Pro Pro Ala Glu His Glu Val Lys Lys Val Thr Leu Gly Asp Thr
            965                 970                 975

Leu Thr Arg Arg Ser Ile Ser Gln Gln Lys Ser Gly Val Ser Ile Thr
            980                 985                 990

Ile Asp Asp Pro Val Arg Thr Ala Gln Val Pro Ser Pro Pro Arg Gly
            995                 1000                1005

Lys Ile Ser Asn Ile Val His Ile Ser Asn Leu Val Arg Pro Phe Thr
    1010                1015                1020

Leu Gly Gln Leu Lys Glu Leu Leu Gly Arg Thr Gly Thr Leu Val Glu
1025                1030                1035                1040

Glu Ala Phe Trp Ile Asp Lys Ile Lys Ser His Cys Phe Val Thr Tyr
                1045                1050                1055

Ser Thr Val Glu Glu Ala Val Ala Thr Arg Thr Ala Leu His Gly Val
            1060                1065                1070

Lys Trp Pro Gln Ser Asn Pro Lys Phe Leu Cys Ala Asp Tyr Ala Glu
            1075                1080                1085

Gln Asp Glu Leu Asp Tyr His Arg Gly Leu Leu Val Asp Arg Pro Ser
            1090                1095                1100

Glu Thr Lys Thr Glu Glu Gln Gly Ile Pro Arg Pro Leu His Pro Pro
1105                1110                1115                1120

Pro Pro Pro Pro Val Gln Pro Pro Gln His Pro Arg Ala Glu Gln Arg
                1125                1130                1135

Glu Gln Glu Arg Ala Val Arg Glu Gln Trp Ala Glu Arg Glu Arg Glu
            1140                1145                1150

Met Glu Arg Arg Glu Arg Thr Arg Ser Glu Arg Glu Trp Asp Arg Asp
            1155                1160                1165

Lys Val Arg Glu Gly Pro Arg Ser Arg Ser Arg Ser Arg Asp Arg Arg
            1170                1175                1180

Arg Lys Glu Arg Ala Lys Ser Lys Glu Lys Lys Ser Glu Lys Lys Glu
1185                1190                1195                1200
```

-continued

Lys Ala Gln Glu Glu Pro Pro Ala Lys Leu Leu Asp Asp Leu Phe Arg
                1205                1210                1215

Lys Thr Lys Ala Ala Pro Cys Ile Tyr Trp Leu Pro Leu Thr Asp Ser
            1220                1225                1230

Gln Ile Val Gln Lys Glu Ala Glu Arg Ala Glu Arg Ala Lys Glu Arg
        1235                1240                1245

Glu Lys Arg Arg Lys Glu Gln Glu Glu Gln Lys Glu Arg Glu
    1250                1255                1260

Lys Glu Ala Glu Arg Glu Arg Asn Arg Gln Leu Glu Arg Glu Lys Arg
1265                1270                1275                1280

Arg Glu His Ser Arg Glu Asp Arg Glu Arg Glu Arg Glu
        1285                1290                1295

Arg Asp Arg Gly Asp Arg Asp Arg Asp Arg Glu Arg Asp Arg Glu Arg
        1300                1305                1310

Gly Arg Glu Arg Asp Arg Arg Asp Thr Lys Arg His Ser Arg Ser Arg
    1315                1320                1325

Ser Arg Ser Thr Pro Val Arg Asp Arg Gly Gly Arg Arg
    1330                1335                1340

<210> SEQ ID NO 2
<211> LENGTH: 583
<212> TYPE: PRT
<213> ORGANISM: Homo sapiens

<400> SEQUENCE: 2

Met Leu Ser Glu Ser Lys Glu Gly Glu Glu Lys Glu Glu Val Thr Met
 1               5                  10                  15

Asp Thr Ser Glu Asn Arg Pro Glu Asn Asp Val Pro Glu Pro Pro Met
            20                  25                  30

Pro Ile Ala Asp Gln Val Ser Asn Asp Asp Arg Pro Glu Gly Ser Val
        35                  40                  45

Glu Asp Glu Glu Lys Lys Glu Ser Ser Leu Pro Lys Ser Phe Lys Arg
    50                  55                  60

Lys Ile Ser Val Val Ser Ala Thr Lys Gly Val Pro Ala Gly Asn Ser
65                  70                  75                  80

Asp Thr Glu Gly Gly Gln Pro Gly Arg Lys Arg Arg Trp Gly Ala Ser
                85                  90                  95

Thr Ala Thr Thr Gln Lys Lys Pro Ser Ile Ser Ile Thr Thr Glu Ser
            100                 105                 110

Leu Lys Ser Leu Ile Pro Asp Ile Lys Pro Leu Ala Gly Gln Glu Ala
        115                 120                 125

Val Val Asp Leu His Ala Asp Asp Ser Arg Ile Ser Glu Asp Glu Thr
    130                 135                 140

Glu Arg Asn Gly Asp Asp Gly Thr His Asp Lys Gly Leu Lys Ile Cys
145                 150                 155                 160

Arg Thr Val Thr Gln Val Val Pro Ala Glu Gly Gln Glu Asn Gly Gln
                165                 170                 175

Arg Glu Glu Glu Glu Glu Lys Glu Pro Glu Ala Glu Pro Pro Val
            180                 185                 190

Pro Pro Gln Val Ser Val Glu Val Ala Leu Pro Pro Ala Glu His
        195                 200                 205

Glu Val Lys Lys Val Thr Leu Gly Asp Thr Leu Thr Arg Arg Ser Ile
    210                 215                 220

Ser Gln Gln Lys Ser Gly Val Ser Ile Thr Ile Asp Asp Pro Val Arg
225                 230                 235                 240

```
Thr Ala Gln Val Pro Ser Pro Pro Arg Gly Lys Ile Ser Asn Ile Val
                245                 250                 255

His Ile Ser Asn Leu Val Arg Pro Phe Thr Leu Gly Gln Leu Lys Glu
            260                 265                 270

Leu Leu Gly Arg Thr Gly Thr Leu Val Glu Glu Ala Phe Trp Ile Asp
        275                 280                 285

Lys Ile Lys Ser His Cys Phe Val Thr Tyr Ser Thr Val Glu Glu Ala
290                 295                 300

Val Ala Thr Arg Thr Ala Leu His Gly Val Lys Trp Pro Gln Ser Asn
305                 310                 315                 320

Pro Lys Phe Leu Cys Ala Asp Tyr Ala Glu Gln Asp Glu Leu Asp Tyr
                325                 330                 335

His Arg Gly Leu Leu Val Asp Arg Pro Ser Glu Thr Lys Thr Glu Glu
            340                 345                 350

Gln Gly Ile Pro Arg Pro Leu His Pro Pro Pro Pro Val Gln
        355                 360                 365

Pro Pro Gln His Pro Arg Ala Glu Gln Arg Glu Gln Glu Arg Ala Val
    370                 375                 380

Arg Glu Gln Trp Ala Glu Arg Glu Arg Glu Met Glu Arg Arg Glu Arg
385                 390                 395                 400

Thr Arg Ser Glu Arg Glu Trp Asp Arg Asp Lys Val Arg Glu Gly Pro
                405                 410                 415

Arg Ser Arg Ser Arg Ser Arg Asp Arg Arg Lys Glu Arg Ala Lys
            420                 425                 430

Ser Lys Glu Lys Lys Ser Glu Lys Lys Glu Lys Ala Gln Glu Glu Pro
        435                 440                 445

Pro Ala Lys Leu Leu Asp Asp Leu Phe Arg Lys Thr Lys Ala Ala Pro
    450                 455                 460

Cys Ile Tyr Trp Leu Pro Leu Thr Asp Ser Gln Ile Val Gln Lys Glu
465                 470                 475                 480

Ala Glu Arg Ala Glu Arg Ala Lys Glu Arg Glu Lys Arg Arg Lys Glu
                485                 490                 495

Gln Glu Glu Glu Gln Lys Glu Arg Glu Lys Glu Ala Glu Arg Glu
            500                 505                 510

Arg Asn Arg Gln Leu Glu Arg Glu Lys Arg Arg Glu His Ser Arg Glu
        515                 520                 525

Arg Asp Arg Glu Arg Glu Arg Glu Arg Asp Arg Gly Asp Arg
    530                 535                 540

Asp Arg Asp Arg Glu Arg Asp Arg Glu Arg Gly Arg Glu Arg Asp Arg
545                 550                 555                 560

Arg Asp Thr Lys Arg His Ser Arg Ser Arg Ser Arg Ser Thr Pro Val
                565                 570                 575

Arg Asp Arg Gly Gly Arg Arg
            580

<210> SEQ ID NO 3
<211> LENGTH: 568
<212> TYPE: PRT
<213> ORGANISM: Homo sapiens

<400> SEQUENCE: 3

Met Asp Thr Ser Glu Asn Arg Pro Glu Asn Asp Val Pro Glu Pro Pro
1               5                   10                  15

Met Pro Ile Ala Asp Gln Val Ser Asn Asp Asp Arg Pro Glu Gly Ser
```

-continued

```
                    20                  25                  30
Val Glu Asp Glu Lys Lys Glu Ser Ser Leu Pro Lys Ser Phe Lys
         35                  40                  45
Arg Lys Ile Ser Val Val Ser Ala Thr Lys Gly Val Pro Ala Gly Asn
     50                  55                  60
Ser Asp Thr Glu Gly Gly Gln Pro Gly Arg Lys Arg Trp Gly Ala
 65                  70                  75                  80
Ser Thr Ala Thr Thr Gln Lys Lys Pro Ser Ile Ser Ile Thr Thr Glu
             85                  90                  95
Ser Leu Lys Ser Leu Ile Pro Asp Ile Lys Pro Leu Ala Gly Gln Glu
                100                 105                 110
Ala Val Val Asp Leu His Ala Asp Asp Ser Arg Ile Ser Glu Asp Glu
            115                 120                 125
Thr Glu Arg Asn Gly Asp Asp Gly Thr His Asp Lys Gly Leu Lys Ile
    130                 135                 140
Cys Arg Thr Val Thr Gln Val Val Pro Ala Glu Gly Gln Glu Asn Gly
145                 150                 155                 160
Gln Arg Glu Glu Glu Glu Glu Lys Glu Pro Glu Ala Glu Pro Pro
                165                 170                 175
Val Pro Pro Gln Val Ser Val Glu Val Ala Leu Pro Pro Ala Glu
            180                 185                 190
His Glu Val Lys Lys Val Thr Leu Gly Asp Thr Leu Thr Arg Arg Ser
            195                 200                 205
Ile Ser Gln Gln Lys Ser Gly Val Ser Ile Thr Ile Asp Asp Pro Val
    210                 215                 220
Arg Thr Ala Gln Val Pro Ser Pro Arg Gly Lys Ile Ser Asn Ile
225                 230                 235                 240
Val His Ile Ser Asn Leu Val Arg Pro Phe Thr Leu Gly Gln Leu Lys
                245                 250                 255
Glu Leu Leu Gly Arg Thr Gly Thr Leu Val Glu Glu Ala Phe Trp Ile
            260                 265                 270
Asp Lys Ile Lys Ser His Cys Phe Val Thr Tyr Ser Thr Val Glu Glu
            275                 280                 285
Ala Val Ala Thr Arg Thr Ala Leu His Gly Val Lys Trp Pro Gln Ser
    290                 295                 300
Asn Pro Lys Phe Leu Cys Ala Asp Tyr Ala Glu Gln Asp Glu Leu Asp
305                 310                 315                 320
Tyr His Arg Gly Leu Leu Val Asp Arg Pro Ser Glu Thr Lys Thr Glu
                325                 330                 335
Glu Gln Gly Ile Pro Arg Pro Leu His Pro Pro Pro Pro Val
            340                 345                 350
Gln Pro Pro Gln His Pro Arg Ala Glu Gln Arg Glu Gln Glu Arg Ala
            355                 360                 365
Val Arg Glu Gln Trp Ala Glu Arg Glu Arg Glu Met Glu Arg Glu
    370                 375                 380
Arg Thr Arg Ser Glu Arg Glu Trp Asp Arg Asp Lys Val Arg Glu Gly
385                 390                 395                 400
Pro Arg Ser Arg Ser Arg Ser Arg Asp Arg Arg Lys Glu Arg Ala
                405                 410                 415
Lys Ser Lys Glu Lys Lys Ser Glu Lys Lys Glu Lys Ala Gln Glu Glu
            420                 425                 430
Pro Pro Ala Lys Leu Leu Asp Asp Leu Phe Arg Lys Thr Lys Ala Ala
            435                 440                 445
```

```
Pro Cys Ile Tyr Trp Leu Pro Leu Thr Asp Ser Gln Ile Val Gln Lys
        450                 455                 460

Glu Ala Glu Arg Ala Glu Arg Ala Lys Glu Arg Lys Arg Arg Lys
465                 470                 475                 480

Glu Gln Glu Glu Glu Gln Lys Glu Arg Glu Lys Glu Ala Glu Arg
                485                 490                 495

Glu Arg Asn Arg Gln Leu Glu Arg Glu Lys Arg Glu His Ser Arg
                500                 505                 510

Glu Arg Asp Arg Glu Arg Glu Arg Glu Arg Asp Arg Gly Asp
            515                 520                 525

Arg Asp Arg Asp Arg Glu Arg Asp Arg Glu Arg Gly Arg Glu Arg Asp
545         530                 535                 540

Arg Arg Asp Thr Lys Arg His Ser Arg Ser Arg Ser Arg Ser Thr Pro
545                 550                 555                 560

Val Arg Asp Arg Gly Gly Arg Arg
                565

<210> SEQ ID NO 4
<211> LENGTH: 107
<212> TYPE: PRT
<213> ORGANISM: Homo sapiens

<400> SEQUENCE: 4

Ser Gly Val Ser Ile Thr Ile Asp Asp Pro Val Arg Thr Ala Gln Val
 1               5                  10                  15

Pro Ser Pro Pro Arg Gly Lys Ile Ser Asn Ile Val His Ile Ser Asn
                20                  25                  30

Leu Val Arg Pro Phe Thr Leu Gly Gln Leu Lys Glu Leu Leu Gly Arg
            35                  40                  45

Thr Gly Thr Leu Val Glu Glu Ala Phe Trp Ile Asp Lys Ile Lys Ser
        50                  55                  60

His Cys Phe Val Thr Tyr Ser Thr Val Glu Glu Ala Val Ala Thr Arg
 65                 70                  75                  80

Thr Ala Leu His Gly Val Lys Trp Pro Gln Ser Asn Pro Lys Phe Leu
                85                  90                  95

Cys Ala Asp Tyr Ala Glu Gln Asp Glu Leu Asp
            100                 105

<210> SEQ ID NO 5
<211> LENGTH: 4936
<212> TYPE: DNA
<213> ORGANISM: Homo sapiens
<220> FEATURE:
<221> NAME/KEY: CDS
<222> LOCATION: (329)..(4351)
<221> NAME/KEY: unsure
<222> LOCATION: 1
<223> OTHER INFORMATION: n is shown to be unsure of exact sequence

<400> SEQUENCE: 5 nctttctct cgaagggcac ccgaagattg tcacgagtcc ttagactcca actactgcgg      60
cagcttccaa atttcctaaa accctaagct gggccagccc ggcagcccac gcacttccgg    120
cctcggaccc gccccaaaca cccagcgccc cagcgcctc atctctaggt ccggaaataa    180
acgaacatct ccgattatgg ttataccagg gtcgagggtt ccgaatata ttcgattcaa    240 agcttcggca agacgaagaa aaccgagcct gaaagcaggg cgagaaaagg ggcgctgcag    300
ggcggatgga aagaattgat tggtaacg atg tgg aga cgg aaa cat ccg agg      352
```

-continued

```
                  Met Trp Arg Arg Lys His Pro Arg
                    1               5 aca tcc gga gga acc cgg gga gtt ctg agt ggt aat cga ggg gta gag      400
Thr Ser Gly Gly Thr Arg Gly Val Leu Ser Gly Asn Arg Gly Val Glu
     10              15                  20 tat ggc agt ggg cgg ggt cat ctc ggt acg ttc gaa ggg cgt tgg cgg      448
Tyr Gly Ser Gly Arg Gly His Leu Gly Thr Phe Glu Gly Arg Trp Arg
 25              30                  35                  40 aaa tta ccg aag atg ccc gaa gcc gtc ggg acg gac ccg agt acc tca      496
Lys Leu Pro Lys Met Pro Glu Ala Val Gly Thr Asp Pro Ser Thr Ser
                 45                  50                  55 cgc aag atg gcg gag ctg gag gag gtg act ctg gac ggg aag cct ctt      544
Arg Lys Met Ala Glu Leu Glu Glu Val Thr Leu Asp Gly Lys Pro Leu
             60                  65                  70 cag gcg ctg cgg gtg acc gac ctg aag gcc gca ctg gag cag cga ggc      592
Gln Ala Leu Arg Val Thr Asp Leu Lys Ala Ala Leu Glu Gln Arg Gly
         75                  80                  85 cta gcc aag agc ggg cag aag agt gcc ctg gtc aag cgg ctc aaa ggg      640
Leu Ala Lys Ser Gly Gln Lys Ser Ala Leu Val Lys Arg Leu Lys Gly
     90                  95                 100 gct cta atg cta gaa aat tta cag aaa cac tca aca ccc cat gct gca      688
Ala Leu Met Leu Glu Asn Leu Gln Lys His Ser Thr Pro His Ala Ala
105             110                 115                 120 ttc cag cca aat tcc cag att ggt gag gaa atg agc cag aac agt ttc      736
Phe Gln Pro Asn Ser Gln Ile Gly Glu Glu Met Ser Gln Asn Ser Phe
                125                 130                 135 ata aaa cag tat ctg gaa aag cag cag gag cta ctt agg cag cgt ctg      784
Ile Lys Gln Tyr Leu Glu Lys Gln Gln Glu Leu Leu Arg Gln Arg Leu
            140                 145                 150 gaa cgt gaa gct cga gaa gct gca gaa ctt gaa gaa gct tca gct gag      832
Glu Arg Glu Ala Arg Glu Ala Ala Glu Leu Glu Glu Ala Ser Ala Glu
        155                 160                 165 tcg gag gac gag atg atc cat cct gag gga gtg gct tcc ctg ctg cct      880
Ser Glu Asp Glu Met Ile His Pro Glu Gly Val Ala Ser Leu Leu Pro
    170                 175                 180 cct gac ttt cag agc agc ctg gag aga cca gag ctg gag ctc agc aga      928
Pro Asp Phe Gln Ser Ser Leu Glu Arg Pro Glu Leu Glu Leu Ser Arg
185                 190                 195                 200 cat tcg ccc aga aaa agc tcc tca att tct gaa gag aaa ggt gac tct      976
His Ser Pro Arg Lys Ser Ser Ser Ile Ser Glu Glu Lys Gly Asp Ser
                205                 210                 215 gat gat gag aaa cca agg aaa gga gaa aga cga tca tct agg gtc aga     1024
Asp Asp Glu Lys Pro Arg Lys Gly Glu Arg Arg Ser Ser Arg Val Arg
            220                 225                 230 cag gca aga gca gct aaa ctg tct gag ggc agc caa cct gct gag gag     1072
Gln Ala Arg Ala Ala Lys Leu Ser Glu Gly Ser Gln Pro Ala Glu Glu
        235                 240                 245 gaa gag gat caa gaa aca cct tcc aga aac cta agg gtc aga gca gat     1120
Glu Glu Asp Gln Glu Thr Pro Ser Arg Asn Leu Arg Val Arg Ala Asp
    250                 255                 260 cga aat ttg aaa aca gag gag gaa gaa gag gag gag gag gag gag gaa     1168
Arg Asn Leu Lys Thr Glu Glu Glu Glu Glu Glu Glu Glu Glu Glu Glu
265                 270                 275                 280 gaa gat gat gaa gaa gag gaa ggt gat gat gag gga caa aaa tct agg     1216
Glu Asp Asp Glu Glu Glu Glu Gly Asp Asp Glu Gly Gln Lys Ser Arg
                285                 290                 295 gag gca cca atc ctg aaa gag ttt aag gaa gaa ggg gaa gag ata cct     1264
Glu Ala Pro Ile Leu Lys Glu Phe Lys Glu Glu Gly Glu Glu Ile Pro
            300                 305                 310
```

-continued

| | |
|---|---|
| aga gta aaa cca gag gag atg atg gat gag aga ccc aaa aca aga tcc<br>Arg Val Lys Pro Glu Glu Met Met Asp Glu Arg Pro Lys Thr Arg Ser<br>    315                     320                  325 | 1312 |
| cag gaa cag gag gtg tta gag aga gga ggg aga ttt aca aga tcc cag<br>Gln Glu Gln Glu Val Leu Glu Arg Gly Gly Arg Phe Thr Arg Ser Gln<br>330                 335                 340 | 1360 |
| gaa gag gct aga aaa agt cat ctg gcc aga cag cag cag gag aag gaa<br>Glu Glu Ala Arg Lys Ser His Leu Ala Arg Gln Gln Gln Glu Lys Glu<br>345                 350                 355                 360 | 1408 |
| atg aaa aca aca tct ccc ctt gag gag gaa gaa aga gaa ata aaa tct<br>Met Lys Thr Thr Ser Pro Leu Glu Glu Glu Glu Arg Glu Ile Lys Ser<br>               365                 370                 375 | 1456 |
| tca caa ggc tta aag gaa aaa tcg aag tct cct tcc cct cct cga ctg<br>Ser Gln Gly Leu Lys Glu Lys Ser Lys Ser Pro Ser Pro Pro Arg Leu<br>         380                   385                 390 | 1504 |
| act gaa gat cga aag aag gcc tca ctt gta gcg ctg cca gag caa act<br>Thr Glu Asp Arg Lys Lys Ala Ser Leu Val Ala Leu Pro Glu Gln Thr<br>               395                 400                 405 | 1552 |
| gcc agc gag gag gag act cct cca cct tta cta aca aag gaa gca tct<br>Ala Ser Glu Glu Glu Thr Pro Pro Pro Leu Leu Thr Lys Glu Ala Ser<br>410                     415                 420 | 1600 |
| tct cca cca cct cat cca cag ctc cat agc gaa gaa gaa ata gag ccc<br>Ser Pro Pro Pro His Pro Gln Leu His Ser Glu Glu Glu Ile Glu Pro<br>425                   430                 435                 440 | 1648 |
| atg gaa ggc cca gcc ccc cct gtc ctc att cag tta tct cct cct aat<br>Met Glu Gly Pro Ala Pro Pro Val Leu Ile Gln Leu Ser Pro Pro Asn<br>                    445                 450                 455 | 1696 |
| aca gat gct gac acc agg gag cta tta gta tct cag cat act gtc cag<br>Thr Asp Ala Asp Thr Arg Glu Leu Leu Val Ser Gln His Thr Val Gln<br>               460                 465                 470 | 1744 |
| ttg gta gga ggc ctg tct cct ttg tca agt cct tca gac acc aaa gca<br>Leu Val Gly Gly Leu Ser Pro Leu Ser Ser Pro Ser Asp Thr Lys Ala<br>         475                   480                 485 | 1792 |
| gaa tct cca gca gag aaa gtg cca gag gag agt gtc ctg cct ctg gtt<br>Glu Ser Pro Ala Glu Lys Val Pro Glu Glu Ser Val Leu Pro Leu Val<br>490                    495                 500 | 1840 |
| cag aaa agc aca ctg gct gac tac tca gcc cag aag gat ctt gaa cct<br>Gln Lys Ser Thr Leu Ala Asp Tyr Ser Ala Gln Lys Asp Leu Glu Pro<br>505                   510                 515                 520 | 1888 |
| gag tca gac aga tct gct cag ccc ctc cct cta aaa att gag gaa tta<br>Glu Ser Asp Arg Ser Ala Gln Pro Leu Pro Leu Lys Ile Glu Glu Leu<br>               525                 530                 535 | 1936 |
| gca ctg gcc aaa gga atc act gaa gaa tgt ctg aaa cag cca tct ttg<br>Ala Leu Ala Lys Gly Ile Thr Glu Glu Cys Leu Lys Gln Pro Ser Leu<br>         540                   545                 550 | 1984 |
| gaa cag aag gaa ggc aga aga gct tct cat acc ctt ctc cca agc cac<br>Glu Gln Lys Glu Gly Arg Arg Ala Ser His Thr Leu Leu Pro Ser His<br>555                    560                 565 | 2032 |
| aga ttg aaa cag tca gct gat tca tcc tct agc cgg tcc tcc tca tct<br>Arg Leu Lys Gln Ser Ala Asp Ser Ser Ser Ser Arg Ser Ser Ser Ser<br>         570                   575                 580 | 2080 |
| tcc tcc tcc agt tct aga tca aga tct cgc tct cct gac agt tca ggt<br>Ser Ser Ser Ser Ser Arg Ser Arg Ser Arg Ser Pro Asp Ser Ser Gly<br>585                    590                 595                 600 | 2128 |
| tct cgg tct cat tca ccg ctc aga tcc aag cag aga gat gta gcc cag<br>Ser Arg Ser His Ser Pro Leu Arg Ser Lys Gln Arg Asp Val Ala Gln<br>               605                 610                 615 | 2176 |
| gca cgt act cat gcc aac cct cgt ggt aga ccc aag atg ggc tcc aga<br>Ala Arg Thr His Ala Asn Pro Arg Gly Arg Pro Lys Met Gly Ser Arg<br>         620                   625                 630 | 2224 |

-continued

| | | |
|---|---|---|
| tca aca tca gag tcc aga tca agg tca cgt tca cgt tct cgt tca gca<br>Ser Thr Ser Glu Ser Arg Ser Arg Ser Arg Ser Arg Ser Arg Ser Ala<br>635                    640                  645 | | 2272 |
| tca agc aac agc aga aaa tct ctg agc cct gga gtc tcc agg gac agc<br>Ser Ser Asn Ser Arg Lys Ser Leu Ser Pro Gly Val Ser Arg Asp Ser<br>650                  655                  660 | | 2320 |
| agc acc agc tat act gaa acc aaa gat ccc tct tct ggt cag gag gtt<br>Ser Thr Ser Tyr Thr Glu Thr Lys Asp Pro Ser Ser Gly Gln Glu Val<br>665                    670                  675                  680 | | 2368 |
| gca act cca cca gtg cca caa ctg cag gtc tgt gag cca aag gag agg<br>Ala Thr Pro Pro Val Pro Gln Leu Gln Val Cys Glu Pro Lys Glu Arg<br>                  685                  690                  695 | | 2416 |
| act tcc acc tcc tca tcc tct gtc caa gca agg cgt ctg agt cag cct<br>Thr Ser Thr Ser Ser Ser Ser Val Gln Ala Arg Arg Leu Ser Gln Pro<br>700                    705                  710 | | 2464 |
| gaa tca gct gaa aag cat gtg acc cag agg tta cag cct gag cgg ggg<br>Glu Ser Ala Glu Lys His Val Thr Gln Arg Leu Gln Pro Glu Arg Gly<br>715                    720                  725 | | 2512 |
| agc cca aag aag tgt gaa gct gaa gag gca gag cca cca gct gcc aca<br>Ser Pro Lys Lys Cys Glu Ala Glu Glu Ala Glu Pro Pro Ala Ala Thr<br>730                    735                  740 | | 2560 |
| cag ccc caa acc tca gag act cag acc tct cat ctg cca gaa tca gaa<br>Gln Pro Gln Thr Ser Glu Thr Gln Thr Ser His Leu Pro Glu Ser Glu<br>745                    750                  755                  760 | | 2608 |
| aga att cat cac act gtt gag gag aag gag gaa gtg acc atg gac aca<br>Arg Ile His His Thr Val Glu Glu Lys Glu Glu Val Thr Met Asp Thr<br>                  765                  770                  775 | | 2656 |
| agt gaa aac aga cct gaa aat gat gtt cca gaa cct ccc atg cct att<br>Ser Glu Asn Arg Pro Glu Asn Asp Val Pro Glu Pro Pro Met Pro Ile<br>                  780                  785                  790 | | 2704 |
| gca gac caa gtc agc aat gat gac cgc ccg gag ggc agt gtt gaa gat<br>Ala Asp Gln Val Ser Asn Asp Asp Arg Pro Glu Gly Ser Val Glu Asp<br>795                    800                  805 | | 2752 |
| gag gag aag aaa gag agc tcg ctg ccc aaa tca ttc aag agg aag atc<br>Glu Glu Lys Lys Glu Ser Ser Leu Pro Lys Ser Phe Lys Arg Lys Ile<br>810                    815                  820 | | 2800 |
| tcc gtt gtc tca gct acc aag ggg gtg cca gct gga aac agt gac aca<br>Ser Val Val Ser Ala Thr Lys Gly Val Pro Ala Gly Asn Ser Asp Thr<br>825                  830                  835                  840 | | 2848 |
| gag ggg ggc cag cct ggt cgg aaa cga cgc tgg gga gcc agc aca gcc<br>Glu Gly Gly Gln Pro Gly Arg Lys Arg Arg Trp Gly Ala Ser Thr Ala<br>                  845                  850                  855 | | 2896 |
| acc aca cag aag aaa cct tcc atc agt atc acc act gaa tca cta aag<br>Thr Thr Gln Lys Lys Pro Ser Ile Ser Ile Thr Thr Glu Ser Leu Lys<br>                  860                  865                  870 | | 2944 |
| agc ctc atc ccc gac atc aaa ccc ctg gcg ggg cag gag gct gtt gtg<br>Ser Leu Ile Pro Asp Ile Lys Pro Leu Ala Gly Gln Glu Ala Val Val<br>875                    880                  885 | | 2992 |
| gat ctt cat gct gat gac tct cgc atc tct gag gat gag aca gag cgt<br>Asp Leu His Ala Asp Asp Ser Arg Ile Ser Glu Asp Glu Thr Glu Arg<br>890                    895                  900 | | 3040 |
| aat ggc gat gat ggg acc cat gac aag ggg ctg aaa ata tgc cgg aca<br>Asn Gly Asp Asp Gly Thr His Asp Lys Gly Leu Lys Ile Cys Arg Thr<br>905                    910                  915                  920 | | 3088 |
| gtc act cag gta gta cct gca gag ggc cag gag aat ggg cag agg gaa<br>Val Thr Gln Val Val Pro Ala Glu Gly Gln Glu Asn Gly Gln Arg Glu<br>                  925                  930                  935 | | 3136 |
| gaa gag gaa gaa gag aag gaa cct gaa gca gaa cct cct gta cct ccc<br>Glu Glu Glu Glu Glu Lys Glu Pro Glu Ala Glu Pro Pro Val Pro Pro | | 3184 |

-continued

|  |  |
|---|---|
| 940 945 950 | |
| cag gtg tca gta gag gtg gcc ttg ccc cca cct gca gag cat gaa gta<br>Gln Val Ser Val Glu Val Ala Leu Pro Pro Pro Ala Glu His Glu Val<br>955        960        965 | 3232 |
| aag aaa gtg act tta gga gat acc tta act cga cgt tcc att agc cag<br>Lys Lys Val Thr Leu Gly Asp Thr Leu Thr Arg Arg Ser Ile Ser Gln<br>970        975        980 | 3280 |
| cag aag tcc gga gtt tcc att acc att gat gac cca gtc cga act gcc<br>Gln Lys Ser Gly Val Ser Ile Thr Ile Asp Asp Pro Val Arg Thr Ala<br>985        990        995        1000 | 3328 |
| cag gtg ccc tcc cca ccc cgg ggc aag att agc aac att gtc cat atc<br>Gln Val Pro Ser Pro Pro Arg Gly Lys Ile Ser Asn Ile Val His Ile<br>      1005        1010        1015 | 3376 |
| tcc aat ttg gtc cgt cct ttc act tta ggc cag cta aag gag ttg ttg<br>Ser Asn Leu Val Arg Pro Phe Thr Leu Gly Gln Leu Lys Glu Leu Leu<br>      1020        1025        1030 | 3424 |
| ggg cgc aca gga acc ttg gtg gaa gag gcc ttc tgg att gac aag atc<br>Gly Arg Thr Gly Thr Leu Val Glu Glu Ala Phe Trp Ile Asp Lys Ile<br>      1035        1040        1045 | 3472 |
| aaa tct cat tgc ttt gta acg tac tca aca gta gag gaa gct gtt gcc<br>Lys Ser His Cys Phe Val Thr Tyr Ser Thr Val Glu Glu Ala Val Ala<br>      1050        1055        1060 | 3520 |
| acc cgc aca gct ctg cac ggg gtc aaa tgg ccc cag tcc aat ccc aaa<br>Thr Arg Thr Ala Leu His Gly Val Lys Trp Pro Gln Ser Asn Pro Lys<br>1065        1070        1075        1080 | 3568 |
| ttc ctt tgt gct gac tat gcc gag caa gat gag ctg gat tat cac cga<br>Phe Leu Cys Ala Asp Tyr Ala Glu Gln Asp Glu Leu Asp Tyr His Arg<br>      1085        1090        1095 | 3616 |
| ggc ctc ttg gtg gac cgt ccc tct gaa act aag aca gag gag cag gga<br>Gly Leu Leu Val Asp Arg Pro Ser Glu Thr Lys Thr Glu Glu Gln Gly<br>      1100        1105        1110 | 3664 |
| ata cca cgg ccc ctg cac ccc cca ccc cca ccc ccg gtc cag cca cca<br>Ile Pro Arg Pro Leu His Pro Pro Pro Pro Pro Val Gln Pro Pro<br>      1115        1120        1125 | 3712 |
| cag cac ccc cgg gca gag cag cgg gag cag gaa cgg gca gtg cgg gaa<br>Gln His Pro Arg Ala Glu Gln Arg Glu Gln Glu Arg Ala Val Arg Glu<br>      1130        1135        1140 | 3760 |
| cag tgg gca gaa cgg gaa cgg gaa atg gag cgg cgg gag cgg act cga<br>Gln Trp Ala Glu Arg Glu Arg Glu Met Glu Arg Arg Glu Arg Thr Arg<br>1145        1150        1155        1160 | 3808 |
| tca gag cgt gaa tgg gat cgg gac aaa gtt cga gaa ggg ccc cgt tcc<br>Ser Glu Arg Glu Trp Asp Arg Asp Lys Val Arg Glu Gly Pro Arg Ser<br>      1165        1170        1175 | 3856 |
| cga tca agg tcc cgt gac cgc cgc cgc aag gaa cgt gcg aag tct aaa<br>Arg Ser Arg Ser Arg Asp Arg Arg Arg Lys Glu Arg Ala Lys Ser Lys<br>      1180        1185        1190 | 3904 |
| gaa aag aag agt gag aag aaa gag aaa gcc cag gag gaa cca cct gcc<br>Glu Lys Lys Ser Glu Lys Lys Glu Lys Ala Gln Glu Glu Pro Pro Ala<br>      1195        1200        1205 | 3952 |
| aag ctg ctg gat gac ctt ttc cga aag acc aag gca gct ccc tgc atc<br>Lys Leu Leu Asp Asp Leu Phe Arg Lys Thr Lys Ala Ala Pro Cys Ile<br>      1210        1215        1220 | 4000 |
| tat tgg ctc cca ctg act gac agc cag atc gtt cag aaa gag gca gag<br>Tyr Trp Leu Pro Leu Thr Asp Ser Gln Ile Val Gln Lys Glu Ala Glu<br>1225        1230        1235        1240 | 4048 |
| cgg gcc gaa cgg gcc aag gag cgg gag aag cgg cga aag gag caa gaa<br>Arg Ala Glu Arg Ala Lys Glu Arg Glu Lys Arg Arg Lys Glu Gln Glu<br>      1245        1250        1255 | 4096 |
| gaa gaa gag caa aag gag cgg gag aag gaa gcc gag cgg gaa cgg aac<br> | 4144 |

```
                                                           -continued

Glu Glu Glu Gln Lys Glu Arg Glu Lys Glu Ala Glu Arg Glu Arg Asn
        1260                1265                1270 cga cag ctg gag cga gag aaa cgt cgg gag cac agt cgg gag agg gac     4192
Arg Gln Leu Glu Arg Glu Lys Arg Arg Glu His Ser Arg Glu Arg Asp
    1275                1280                1285 agg gag aga gag aga gaa agg gag cgg gac agg ggg gac cga gat cgg     4240
Arg Glu Arg Glu Arg Glu Arg Glu Arg Asp Arg Gly Asp Arg Asp Arg
1290                1295                1300 gat agg gaa agg gac cga gaa cga ggc agg gaa agg gat cgc agg gac     4288
Asp Arg Glu Arg Asp Arg Glu Arg Gly Arg Glu Arg Asp Arg Arg Asp
1305                1310                1315                1320 acc aag cgc cac agc aga agc cgg agt cgg agc aca cct gtg cgg gac     4336
Thr Lys Arg His Ser Arg Ser Arg Ser Arg Ser Thr Pro Val Arg Asp
            1325                1330                1335 cgg ggt ggg cgc cgc tagctgggaa aacactagag ctgcaggtac cagccactcg     4391
Arg Gly Gly Arg Arg
        1340 gccccagggg gttatggcca cagagggata ggcacagtct ccaccaccct ggagccaagg   4451 gtctttcaca tcacctatcc ctacatacat accaaatgga aaagtggcca tccttttccc   4511 cccaaacaca ccccCttaac ctatctcttg ggacttagcc cgaccctccc tctcatttcc   4571 cattaagtct gagaggcaag agctaggtta ggcaaggagg tggttggcca gagatgggga   4631 acagccaggt gccccagtcc tctgattttt cctccatcct gcttaccacc tccctgggta   4691 cttacagcct tctcttggga acagccgggc ccaggactgg gtcacctatg agctgaatca   4751 gcatctcctc ctgagtccca gggccctgc agttcccagt ctcttctgtc ctgcagccct    4811 tgcctctttc ccacaggttc cactttatat ccacctttc cttttgttca atttttattt    4871 ttatttttt tattattaaa tgatgtggtc tatggaaaaa aaataaaaa tctgacttag     4931 ttttt                                                               4936
```

<210> SEQ ID NO 6
<211> LENGTH: 2528
<212> TYPE: DNA
<213> ORGANISM: Homo sapiens
<220> FEATURE:
<221> NAME/KEY: CDS
<222> LOCATION: (195)..(1943)
<221> NAME/KEY: unsure
<222> LOCATION: 20, 104, 114, 148, 156
<223> OTHER INFORMATION: n is shown to be unsure of exact sequence

<400> SEQUENCE: 6

```
gggtccgggc cccccctcgn ggtcgacggt atcgataagc ttgatatccg aattcgctgc     60
cgctccgcca atacaataga gccagccact accagcagcc tggncctctt actncttctc    120
cagagagacc aatccagccg aactcggngt ttgccnaagg gataaacagc acttccaggg    180
ggagaaaaaa aatc atg tta tca gaa agc aaa gaa ggt gag gag aag gag      230
              Met Leu Ser Glu Ser Lys Glu Gly Glu Glu Lys Glu
                1               5                   10 gaa gtg acc atg gac aca agt gaa aac aga cct gaa aat gat gtt cca      278
Glu Val Thr Met Asp Thr Ser Glu Asn Arg Pro Glu Asn Asp Val Pro
        15                  20                  25 gaa cct ccc atg cct att gca gac caa gtc agc aat gat gac cgc ccg      326
Glu Pro Pro Met Pro Ile Ala Asp Gln Val Ser Asn Asp Asp Arg Pro
    30                  35                  40 gag ggc agt gtt gaa gat gag gag aag aaa gag agc tcg ctg ccc aaa      374
Glu Gly Ser Val Glu Asp Glu Glu Lys Lys Glu Ser Ser Leu Pro Lys
45                  50                  55                  60
```

```
                                                        -continued tca ttc aag agg aag atc tcc gtt gtc tca gct acc aag ggg gtg cca      422
Ser Phe Lys Arg Lys Ile Ser Val Val Ser Ala Thr Lys Gly Val Pro
            65                  70                  75 gct gga aac agt gac aca gag ggg ggc cag cct ggt cgg aaa cga cgc      470
Ala Gly Asn Ser Asp Thr Glu Gly Gly Gln Pro Gly Arg Lys Arg Arg
        80                  85                  90 tgg gga gcc agc aca gcc acc aca cag aag aaa cct tcc atc agt atc      518
Trp Gly Ala Ser Thr Ala Thr Thr Gln Lys Lys Pro Ser Ile Ser Ile
        95                  100                 105 acc act gaa tca cta aag agc ctc atc ccc gac atc aaa ccc ctg gcg      566
Thr Thr Glu Ser Leu Lys Ser Leu Ile Pro Asp Ile Lys Pro Leu Ala
    110                 115                 120 ggg cag gag gct gtt gtg gat ctt cat gct gat gac tct cgc atc tct      614
Gly Gln Glu Ala Val Val Asp Leu His Ala Asp Asp Ser Arg Ile Ser
125                 130                 135                 140 gag gat gag aca gag cgt aat ggc gat gat ggg acc cat gac aag ggg      662
Glu Asp Glu Thr Glu Arg Asn Gly Asp Asp Gly Thr His Asp Lys Gly
                145                 150                 155 ctg aaa ata tgc cgg aca gtc act cag gta gta cct gca gag ggc cag      710
Leu Lys Ile Cys Arg Thr Val Thr Gln Val Val Pro Ala Glu Gly Gln
                160                 165                 170 gag aat ggg cag agg gaa gaa gag gaa gaa gag aag gaa cct gaa gca      758
Glu Asn Gly Gln Arg Glu Glu Glu Glu Glu Glu Lys Glu Pro Glu Ala
            175                 180                 185 gaa cct cct gta cct ccc cag gtg tca gta gag gtg gcc ttg ccc cca      806
Glu Pro Pro Val Pro Pro Gln Val Ser Val Glu Val Ala Leu Pro Pro
        190                 195                 200 cct gca gag cat gaa gta aag aaa gtg act tta gga gat acc tta act      854
Pro Ala Glu His Glu Val Lys Lys Val Thr Leu Gly Asp Thr Leu Thr
205                 210                 215                 220 cga cgt tcc att agc cag cag aag tcc gga gtt tcc att acc att gat      902
Arg Arg Ser Ile Ser Gln Gln Lys Ser Gly Val Ser Ile Thr Ile Asp
                225                 230                 235 gac cca gtc cga act gcc cag gtg ccc tcc cca ccc cgg ggc aag att      950
Asp Pro Val Arg Thr Ala Gln Val Pro Ser Pro Pro Arg Gly Lys Ile
                240                 245                 250 agc aac att gtc cat atc tcc aat ttg gtc cgt cct ttc act tta ggc      998
Ser Asn Ile Val His Ile Ser Asn Leu Val Arg Pro Phe Thr Leu Gly
            255                 260                 265 cag cta aag gag ttg ttg ggg cgc aca gga acc ttg gtg gaa gag gcc     1046
Gln Leu Lys Glu Leu Leu Gly Arg Thr Gly Thr Leu Val Glu Glu Ala
        270                 275                 280 ttc tgg att gac aag atc aaa tct cat tgc ttt gta acg tac tca aca     1094
Phe Trp Ile Asp Lys Ile Lys Ser His Cys Phe Val Thr Tyr Ser Thr
285                 290                 295                 300 gta gag gaa gct gtt gcc acc cgc aca gct ctg cac ggg gtc aaa tgg     1142
Val Glu Glu Ala Val Ala Thr Arg Thr Ala Leu His Gly Val Lys Trp
                305                 310                 315 ccc cag tcc aat ccc aaa ttc ctt tgt gct gac tat gcc gag caa gat     1190
Pro Gln Ser Asn Pro Lys Phe Leu Cys Ala Asp Tyr Ala Glu Gln Asp
                320                 325                 330 gag ctg gat tat cac cga ggc ctc ttg gtg gac cgt ccc tct gaa act     1238
Glu Leu Asp Tyr His Arg Gly Leu Leu Val Asp Arg Pro Ser Glu Thr
            335                 340                 345 aag aca gag gag cag gga ata cca cgg ccc ctg cac ccc cca ccc cca     1286
Lys Thr Glu Glu Gln Gly Ile Pro Arg Pro Leu His Pro Pro Pro Pro
        350                 355                 360 ccc ccg gtc cag cca cca cag cac ccc cgg gca gag cag cgg gag cag     1334
Pro Pro Val Gln Pro Pro Gln His Pro Arg Ala Glu Gln Arg Glu Gln
365                 370                 375                 380
```

```
gaa cgg gca gtg cgg gaa cag tgg gca gaa cgg gaa cgg gaa atg gag      1382
Glu Arg Ala Val Arg Glu Gln Trp Ala Glu Arg Glu Arg Glu Met Glu
                385                 390                 395 cgg cgg gag cgg act cga tca gag cgt gaa tgg gat cgg gac aaa gtt      1430
Arg Arg Glu Arg Thr Arg Ser Glu Arg Glu Trp Asp Arg Asp Lys Val
    400                 405                 410 cga gaa ggg ccc cgt tcc cga tca agg tcc cgt gac cgc cgc cgc aag      1478
Arg Glu Gly Pro Arg Ser Arg Ser Arg Ser Arg Asp Arg Arg Arg Lys
415                 420                 425 gaa cgt gcg aag tct aaa gaa aag aag agt gag aag aaa gag aaa gcc      1526
Glu Arg Ala Lys Ser Lys Glu Lys Lys Ser Glu Lys Lys Glu Lys Ala
        430                 435                 440 cag gag gaa cca cct gcc aag ctg ctg gat gac ctt ttc cga aag acc      1574
Gln Glu Glu Pro Pro Ala Lys Leu Leu Asp Asp Leu Phe Arg Lys Thr
445                 450                 455                 460 aag gca gct ccc tgc atc tat tgg ctc cca ctg act gac agc cag atc      1622
Lys Ala Ala Pro Cys Ile Tyr Trp Leu Pro Leu Thr Asp Ser Gln Ile
                465                 470                 475 gtt cag aaa gag gca gag cgg gcc gaa cgg gcc aag gag cgg gag aag      1670
Val Gln Lys Glu Ala Glu Arg Ala Glu Arg Ala Lys Glu Arg Glu Lys
                480                 485                 490 cgg cga aag gag caa gaa gaa gaa gag caa aag gag cgg gag aag gaa      1718
Arg Arg Lys Glu Gln Glu Glu Glu Glu Gln Lys Glu Arg Glu Lys Glu
    495                 500                 505 gcc gag cgg gaa cgg aac cga cag ctg gag cga gag aaa cgt cgg gag      1766
Ala Glu Arg Glu Arg Asn Arg Gln Leu Glu Arg Glu Lys Arg Arg Glu
510                 515                 520 cac agt cgg gag agg gac agg gag aga gag aga gaa agg gag cgg gac      1814
His Ser Arg Glu Arg Asp Arg Glu Arg Glu Arg Glu Arg Glu Arg Asp
525                 530                 535                 540 agg ggg gac cga gat cgg gat agg gaa agg gac cga gaa cga ggc agg      1862
Arg Gly Asp Arg Asp Arg Asp Arg Glu Arg Asp Arg Glu Arg Gly Arg
                545                 550                 555 gaa agg gat cgc agg gac acc aag cgc cac agc aga agc cgg agt cgg      1910
Glu Arg Asp Arg Arg Asp Thr Lys Arg His Ser Arg Ser Arg Ser Arg
                560                 565                 570 agc aca cct gtg cgg gac cgg ggt ggg cgc cgc tagctgggaa aacactagag    1963
Ser Thr Pro Val Arg Asp Arg Gly Gly Arg Arg
    575                 580 ctgcaggtac cagccactcg gccccagggg gttatggcca cagagggata ggcacagtct    2023
ccaccaccct ggagccaagg gtctttcaca tcacctatcc ctacatacat accaaatgga    2083
aaagtggcca tccttttccc cccaaacaca ccccttaac  ctatctcttg ggacttagcc    2143
cgaccctccc tctcatttcc cattaagtct gagaggcaag agctaggtta ggcaaggagg    2203
tggttggcca gagatgggga acagccaggt gccccagtcc tctgattttt cctccatcct    2263
gcttaccacc tccctgggta cttacagcct tctcttggga acagccgggg ccaggactgg    2323
gtcacctatg agctgaatca gcatctcctc ctgagtccca gggcccctgc agttcccagt    2383
ctcttctgtc ctgcagccct tgcctctttc ccacaggttc cactttatat ccacctttc    2443 cttttgttca atttttattt ttatttttt tattattaaa tgatgtggtc tatggaaaaa    2503
aaaataaaaa tctgacttag ttttt                                          2528

<210> SEQ ID NO 7
<211> LENGTH: 2497
<212> TYPE: DNA
<213> ORGANISM: Homo sapiens
<220> FEATURE:
```

-continued

```
<221> NAME/KEY: CDS
<222> LOCATION: (158)..(1861)

<400> SEQUENCE: 7
ggcaagatgg ctcccctgca tgtctccggc tgatcgctgc cgctccgcca atacaataga      60
gccagccact accagcagcc tggccctctt cctccttctc cagagagacc aatccagccg     120
aactcggggt ttgcctgagg agaaggagga agtgacc atg gac aca agt gaa aac      175
                                        Met Asp Thr Ser Glu Asn
                                          1               5 aga cct gaa aat gat gtt cca gaa cct ccc atg cct att gca gac caa       223
Arg Pro Glu Asn Asp Val Pro Glu Pro Pro Met Pro Ile Ala Asp Gln
              10                  15                  20 gtc agc aat gat gac cgc ccg gag ggc agt gtt gaa gat gag gag aag       271
Val Ser Asn Asp Asp Arg Pro Glu Gly Ser Val Glu Asp Glu Glu Lys
         25                  30                  35 aaa gag agc tcg ctg ccc aaa tca ttc aag agg aag atc tcc gtt gtc       319
Lys Glu Ser Ser Leu Pro Lys Ser Phe Lys Arg Lys Ile Ser Val Val
 40                  45                  50 tca gct acc aag ggg gtg cca gct gga aac agt gac aca gag ggg ggc       367
Ser Ala Thr Lys Gly Val Pro Ala Gly Asn Ser Asp Thr Glu Gly Gly
 55                  60                  65                  70 cag cct ggt cgg aaa cga cgc tgg gga gcc agc aca gcc acc aca cag       415
Gln Pro Gly Arg Lys Arg Arg Trp Gly Ala Ser Thr Ala Thr Thr Gln
             75                  80                  85 aaa aaa cct tcc atc agt atc acc act gaa tca cta aag agc ctc atc       463
Lys Lys Pro Ser Ile Ser Ile Thr Thr Glu Ser Leu Lys Ser Leu Ile
         90                  95                 100 ccc gac atc aaa ccc ctg gcg ggg cag gag gct gtt gtg gat ctt cat       511
Pro Asp Ile Lys Pro Leu Ala Gly Gln Glu Ala Val Val Asp Leu His
    105                 110                 115 gct gat gac tct cgc atc tct gag gat gag aca gag cgt aat ggc gat       559
Ala Asp Asp Ser Arg Ile Ser Glu Asp Glu Thr Glu Arg Asn Gly Asp
120                 125                 130 gat ggg acc cat gac aag ggg ctg aaa ata tgc cgg aca gtc act cag       607
Asp Gly Thr His Asp Lys Gly Leu Lys Ile Cys Arg Thr Val Thr Gln
135                 140                 145                 150 gta gta cct gca gag ggc cag gag aat ggg cag agg gaa gaa gag gaa       655
Val Val Pro Ala Glu Gly Gln Glu Asn Gly Gln Arg Glu Glu Glu Glu
                155                 160                 165 gaa gag aag gaa cct gaa gca gaa cct cct gta cct ccc cag gtg tca       703
Glu Glu Lys Glu Pro Glu Ala Glu Pro Pro Val Pro Pro Gln Val Ser
            170                 175                 180 gta gag gtg gcc ttg ccc cca cct gca gag cat gaa gta aag aaa gtg       751
Val Glu Val Ala Leu Pro Pro Pro Ala Glu His Glu Val Lys Lys Val
        185                 190                 195 act tta gga gat acc tta act cga cgt tcc att agc cag cag aag tcc       799
Thr Leu Gly Asp Thr Leu Thr Arg Arg Ser Ile Ser Gln Gln Lys Ser
    200                 205                 210 gga gtt tcc att acc att gat gac cca gtc cga act gcc cag gtg ccc       847
Gly Val Ser Ile Thr Ile Asp Asp Pro Val Arg Thr Ala Gln Val Pro
215                 220                 225                 230 tcc cca ccc cgg ggc aag att agc aac att gtc cat atc tcc aat ttg       895
Ser Pro Pro Arg Gly Lys Ile Ser Asn Ile Val His Ile Ser Asn Leu
                235                 240                 245 gtc cgt cct ttc act tta ggc cag cta aag gag ttg ttg ggg cgc aca       943
Val Arg Pro Phe Thr Leu Gly Gln Leu Lys Glu Leu Leu Gly Arg Thr
            250                 255                 260 gga acc ttg gtg gaa gag gcc ttc tgg att gac aag atc aaa tct cat       991
Gly Thr Leu Val Glu Glu Ala Phe Trp Ile Asp Lys Ile Lys Ser His
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 265 |     |     |     | 270 |     |     |     | 275 |     |     |     |     |      |
| tgc | ttt | gta | acg | tac | tca | aca | gta | gag | gaa | gct | gtt | gcc | acc | cgc | aca | 1039 |
| Cys | Phe | Val | Thr | Tyr | Ser | Thr | Val | Glu | Glu | Ala | Val | Ala | Thr | Arg | Thr |      |
|     | 280 |     |     |     | 285 |     |     |     | 290 |     |     |     |     |     |     |      |
| gct | ctg | cac | ggg | gtc | aaa | tgg | ccc | cag | tcc | aat | ccc | aaa | ttc | ctt | tgt | 1087 |
| Ala | Leu | His | Gly | Val | Lys | Trp | Pro | Gln | Ser | Asn | Pro | Lys | Phe | Leu | Cys |      |
| 295 |     |     |     | 300 |     |     |     | 305 |     |     |     |     |     |     | 310 |      |
| gct | gac | tat | gcc | gag | caa | gat | gag | ctg | gat | tat | cac | cga | ggc | ctc | ttg | 1135 |
| Ala | Asp | Tyr | Ala | Glu | Gln | Asp | Glu | Leu | Asp | Tyr | His | Arg | Gly | Leu | Leu |      |
|     |     |     |     | 315 |     |     |     |     | 320 |     |     |     |     | 325 |     |      |
| gtg | gac | cgt | ccc | tct | gaa | act | aag | aca | gag | gag | cag | gga | ata | cca | cgg | 1183 |
| Val | Asp | Arg | Pro | Ser | Glu | Thr | Lys | Thr | Glu | Glu | Gln | Gly | Ile | Pro | Arg |      |
|     |     | 330 |     |     |     |     | 335 |     |     |     |     | 340 |     |     |     |      |
| ccc | ctg | cac | ccc | cca | ccc | cca | ccc | ccg | gtc | cag | cca | cca | cag | cac | ccc | 1231 |
| Pro | Leu | His | Pro | Pro | Pro | Pro | Pro | Pro | Val | Gln | Pro | Pro | Gln | His | Pro |      |
| 345 |     |     |     |     | 350 |     |     |     |     | 355 |     |     |     |     |     |      |
| cgg | gca | gag | cag | cgg | gag | cag | gaa | cgg | gca | gtg | cgg | gaa | cag | tgg | gca | 1279 |
| Arg | Ala | Glu | Gln | Arg | Glu | Gln | Glu | Arg | Ala | Val | Arg | Glu | Gln | Trp | Ala |      |
|     | 360 |     |     |     |     | 365 |     |     |     |     | 370 |     |     |     |     |      |
| gaa | cgg | gaa | cgg | gaa | atg | gag | cgg | cgg | gag | cgg | act | cga | tca | gag | cgt | 1327 |
| Glu | Arg | Glu | Arg | Glu | Met | Glu | Arg | Arg | Glu | Arg | Thr | Arg | Ser | Glu | Arg |      |
| 375 |     |     |     |     | 380 |     |     |     |     | 385 |     |     |     |     | 390 |      |
| gaa | tgg | gat | cgg | gac | aaa | gtt | cga | gaa | ggg | ccc | cgt | tcc | cga | tca | agg | 1375 |
| Glu | Trp | Asp | Arg | Asp | Lys | Val | Arg | Glu | Gly | Pro | Arg | Ser | Arg | Ser | Arg |      |
|     |     |     | 395 |     |     |     |     | 400 |     |     |     |     | 405 |     |     |      |
| tcc | cgt | gac | cgc | cgc | cgc | aag | gaa | cgt | gcg | aag | tct | aaa | gaa | aag | aag | 1423 |
| Ser | Arg | Asp | Arg | Arg | Arg | Lys | Glu | Arg | Ala | Lys | Ser | Lys | Glu | Lys | Lys |      |
|     |     | 410 |     |     |     |     | 415 |     |     |     |     | 420 |     |     |     |      |
| agt | gag | aag | aaa | gag | aaa | gcc | cag | gag | gaa | cca | cct | gcc | aag | ctg | ctg | 1471 |
| Ser | Glu | Lys | Lys | Glu | Lys | Ala | Gln | Glu | Glu | Pro | Pro | Ala | Lys | Leu | Leu |      |
|     | 425 |     |     |     |     | 430 |     |     |     |     | 435 |     |     |     |     |      |
| gat | gac | ctt | ttc | cga | aag | acc | aag | gca | gct | ccc | tgc | atc | tat | tgg | ctc | 1519 |
| Asp | Asp | Leu | Phe | Arg | Lys | Thr | Lys | Ala | Ala | Pro | Cys | Ile | Tyr | Trp | Leu |      |
| 440 |     |     |     |     | 445 |     |     |     |     | 450 |     |     |     |     |     |      |
| cca | ctg | act | gac | agc | cag | atc | gtt | cag | aaa | gag | gca | gag | cgg | gcc | gaa | 1567 |
| Pro | Leu | Thr | Asp | Ser | Gln | Ile | Val | Gln | Lys | Glu | Ala | Glu | Arg | Ala | Glu |      |
| 455 |     |     |     |     | 460 |     |     |     |     | 465 |     |     |     |     | 470 |      |
| cgg | gcc | aag | gag | cgg | gag | aag | cgg | cga | aag | gag | caa | gaa | gaa | gaa | gag | 1615 |
| Arg | Ala | Lys | Glu | Arg | Glu | Lys | Arg | Arg | Lys | Glu | Gln | Glu | Glu | Glu | Glu |      |
|     |     |     | 475 |     |     |     |     | 480 |     |     |     |     | 485 |     |     |      |
| caa | aag | gag | cgg | gag | aag | gaa | gcc | gag | cgg | gaa | cgg | aac | cga | cag | ctg | 1663 |
| Gln | Lys | Glu | Arg | Glu | Lys | Glu | Ala | Glu | Arg | Glu | Arg | Asn | Arg | Gln | Leu |      |
|     |     | 490 |     |     |     |     | 495 |     |     |     |     | 500 |     |     |     |      |
| gag | cga | gag | aaa | cgt | cgg | gag | cac | agt | cgg | gag | agg | gac | agg | gag | aga | 1711 |
| Glu | Arg | Glu | Lys | Arg | Arg | Glu | His | Ser | Arg | Glu | Arg | Asp | Arg | Glu | Arg |      |
|     | 505 |     |     |     |     | 510 |     |     |     |     | 515 |     |     |     |     |      |
| gag | aga | gaa | agg | gag | cgg | gac | agg | ggg | gac | cga | gat | cgg | gat | agg | gaa | 1759 |
| Glu | Arg | Glu | Arg | Glu | Arg | Asp | Arg | Gly | Asp | Arg | Asp | Arg | Asp | Arg | Glu |      |
| 520 |     |     |     |     | 525 |     |     |     |     | 530 |     |     |     |     |     |      |
| agg | gac | cga | gaa | cga | ggc | agg | gaa | agg | gat | cgc | agg | gac | acc | aag | cgc | 1807 |
| Arg | Asp | Arg | Glu | Arg | Gly | Arg | Glu | Arg | Asp | Arg | Arg | Asp | Thr | Lys | Arg |      |
| 535 |     |     |     |     | 540 |     |     |     |     | 545 |     |     |     |     | 550 |      |
| cac | agc | aga | agc | cgg | agt | cgg | agc | aca | cct | gtg | cgg | gac | cgg | ggt | ggg | 1855 |
| His | Ser | Arg | Ser | Arg | Ser | Arg | Ser | Thr | Pro | Val | Arg | Asp | Arg | Gly | Gly |      |
|     |     |     |     | 555 |     |     |     |     | 560 |     |     |     |     | 565 |     |      |
| cgc | cgc | tagctggaa | | aacactagag | | ctgcaggtac | | cagccactcg | | gccccagggg | | | | | | 1911 |
| Arg | Arg | | | | | | | | | | | | | | | | gttatggcca cagagggata ggcacagtct ccaccaccct ggagccaagg gtctttcaca 1971

```
tcacctatcc ctacatacat accaaatgga aaagtggcca tccttttccc cccaaacaca    2031 ccccccttaac ctatctcttg ggacttagcc cgacccttccc tctcatttcc cattaagtct   2091
gagaggcaag agctaggtta ggcaaggagg tggttggcca gagatgggga acagccaggt    2151
gccccagtcc tctgattttt cctccatcct gcttaccacc tccctgggta cttacagcct    2211
tctcttggga acagccgggg ccaggactgg gtcacctatg agctgaatca gcatctcctc    2271
ctgagtccca gggcccctgc agttcccagt ctcttctgtc ctgcagccct tgcctctttc    2331
ccacaggttc cactttatat ccaccttttc cttttgttca attttttattt ttattttttt    2391 tattattaaa tgatgtggtc tatggaaaaa aaataaaaa tctgacttag ttttaaaaaa     2451
aaaaaaaaaa aaaaaaaaaa aaaaaaaaaa aaaaaaaaaa aaaaaa                   2497
```

<210> SEQ ID NO 8
<211> LENGTH: 321
<212> TYPE: DNA
<213> ORGANISM: Homo sapiens

<400> SEQUENCE: 8

```
tccggagttt ccattaccat tgatgaccca gtccgaactg cccaggtgcc ctccccaccc      60
cggggcaaga ttagcaacat tgtccatatc tccaatttgg tccgtccttt cactttaggc    120
cagctaaagg agttgttggg gcgcacagga accttggtgg aagaggcctt ctggattgac    180
aagatcaaat ctcattgctt tgtaacgtac tcaacagtag aggaagctgt tgccacccgc    240
acagctctgc acgggtcaa atggccccag tccaatccca aattcctttg tgctgactat    300
gccgagcaag atgagctgga t                                              321
```

<210> SEQ ID NO 9
<211> LENGTH: 8
<212> TYPE: PRT
<213> ORGANISM: Homo sapiens

<400> SEQUENCE: 9

```
Met Leu Ser Glu Ser Lys Glu Gly
1               5
```

<210> SEQ ID NO 10
<211> LENGTH: 74
<212> TYPE: PRT
<213> ORGANISM: Homo sapiens

<400> SEQUENCE: 10

```
Val His Ile Ser Asn Leu Val Arg Pro Phe Thr Leu Gly Gln Leu Lys
1               5                   10                  15

Glu Leu Ile Gly Arg Thr Gly Thr Leu Val Glu Glu Ala Phe Trp Ile
            20                  25                  30

Asp Lys Ile Lys Ser His Cys Phe Val Thr Tyr Ser Thr Val Glu Glu
        35                  40                  45

Ala Val Ala Thr Arg Thr His Gly Val Lys Trp Pro Gln Ser Asn Pro
    50                  55                  60

Lys Phe Leu Cys Ala Asp Tyr Ala Glu Gln
65                  70
```

<210> SEQ ID NO 11
<211> LENGTH: 77
<212> TYPE: PRT
<213> ORGANISM: Drosophila melanogaster

<400> SEQUENCE: 11

-continued

```
Leu Tyr Val Thr Asn Leu Pro Arg Thr Ile Thr Asp Asp Gln Leu Asp
1               5                   10                  15

Thr Ile Phe Gly Lys Tyr Gly Ser Ile Val Gln Lys Asn Ile Leu Arg
            20                  25                  30

Asp Lys Leu Thr Gly Arg Pro Arg Gly Val Ala Phe Val Arg Tyr Asn
        35              40                  45

Lys Arg Glu Glu Ala Gln Glu Ala Ile Ser Asn Asn Val Ile Pro Glu
    50              55                  60

Gly Gly Ser Gln Pro Leu Ser Val Arg Leu Ala Glu Glu
65              70                  75
```